United States Patent [19]

Rempfler

[11] Patent Number: 5,154,751

[45] Date of Patent: Oct. 13, 1992

[54] HERBICIDAL UREA COMPOUNDS AND COMPOSITIONS

[75] Inventor: Hermann Rempfler, Ettingen, Switzerland

[73] Assignee: Ciba-Geigy Corporation, Ardsley, N.Y.

[21] Appl. No.: 530,711

[22] Filed: May 30, 1990

[30] Foreign Application Priority Data

Jun. 2, 1989 [CH] Switzerland ............... 2083/89

[51] Int. Cl.$^5$ ............... A01N 43/40; C07D 213/75
[52] U.S. Cl. ............... 71/94; 71/90; 546/297; 546/306
[58] Field of Search ............... 546/300, 287, 289, 296, 546/297, 283, 268, 306; 71/94, 90

[56] References Cited

U.S. PATENT DOCUMENTS

| | | | |
|---|---|---|---|
| 2,802,008 | 8/1957 | Burtner | 260/295 |
| 3,495,969 | 1/1970 | Driscoll | 71/94 |
| 4,279,639 | 7/1981 | Okamoto | 71/94 |
| 4,782,071 | 11/1988 | Butler et al. | 514/353 |
| 4,966,622 | 10/1990 | Rempfler | 71/92 |
| 4,973,690 | 11/1990 | Rempfler | 544/279 |
| 4,999,046 | 3/1991 | Rempfler | 71/92 |

FOREIGN PATENT DOCUMENTS

| | | |
|---|---|---|
| 0010770 | 5/1980 | European Pat. Off. |
| 0031257 | 7/1981 | European Pat. Off. |
| 0292990 | 11/1988 | European Pat. Off. |
| 0384311 | 8/1990 | European Pat. Off. |
| 3731626 | 3/1989 | Fed. Rep. of Germany |

OTHER PUBLICATIONS

Chem. Abstract, 108: 150315u, 1988.
Hackh's Chemical Dictionary 4th Edition (1969) p. 326.
McGraw-Hill Dictionary 3rd Edition (1984) p. 762.

*Primary Examiner*—Robert W. Ramsuer
*Assistant Examiner*—Jacqueline Haley
*Attorney, Agent, or Firm*—Kevin T. Mansfield; Edward McC. Roberts

[57] ABSTRACT

The invention relates to novel compositions having herbicidal and plant growth regulating properties and containing, as active ingredient, a compound of formula I

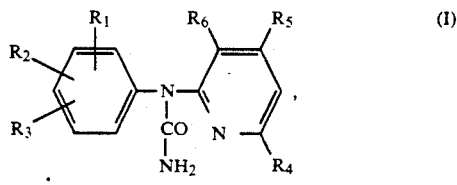

wherein $R_1$ to $R_6$ are as defined in the description, to novel compounds of formula I and intermediates, and to the preparation thereof.

28 Claims, No Drawings

HERBICIDAL UREA COMPOUNDS AND COMPOSITIONS

The present invention relates to novel N-phenyl-N-pyridin-2-ylureas having herbicidal and plant growth regulating properties, to agrochemical compositions which contain these compounds as active ingredients, to the use of the novel ureas for controlling weeds or for regulating plant growth, as well as to the preparation of said novel compounds. The invention further relates to novel intermediates and to the preparation thereof.

N-Phenyl-N-pyridin-2- and -3-ylureas which are unsubstituted in the pyridine moiety system and which have cardiovascular properties are disclosed in U.S. Pat. No. 2,802,008. It has now been found in contradistrinction thereto that specific substituted N-phenyl-N-pyridine-2-ylureas have herbicidal and plant growth regulating properties.

Specifically, the present invention relates to herbicidal and/or plant growth regulating compositions which contain, as active ingredient, a urea of formula I

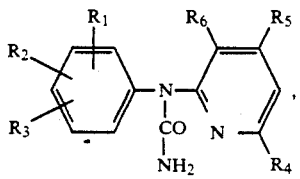

wherein $R_1$, $R_2$ and $R_3$ are each independently of one another hydrogen; nitro; cyano; halogen; $C_1$–$C_4$alkyl; $C_1$–$C_4$alkyl-$S(O)_n$-; $C_1$–$C_4$alkoxy; $C_1$–$C_4$haloalkyl; $C_1$–$C_4$haloalkoxy; $C_1$–$C_4$haloalkyl-$S(O)_n$-; $C_1$–$C_4$alkoxycarbonyl; $C_1$–$C_4$alkylcarbonyl; carbamoyl; mono-$C_1$–$C_4$alkylcarbamoyl; or di-$C_1$–$C_4$alkylcarbamoyl;

$R_4$ and $R_5$ are each independently of the other hydrogen; $C_1$–$C_4$alkyl; $C_1$–$C_4$alkyl-$S(O)_n$-; $C_1$–$C_4$alkoxy; $C_1$–$C_4$haloalkyl; $C_1$–$C_4$haloalkoxy; $C_1$–$C_4$haloalkyl-$S(O)_n$-; unsubstituted phenyl or phenyl which is substituted by one to three identical or different members of the group consisting of $C_1$–$C_4$alkyl, halogen, $C_1$–$C_4$alkoxy, $C_1$–$C_4$haloalkyl, nitro or cyano; furanyl; thiophenyl; $C_3$–$C_6$cycloalkyl; $C_1$–$C_4$alkoxycarbonyl; $C_1$–$C_4$alkoxy-$C_1$–$C_4$alkyl; $C_1$–$C_4$alkoxycarbonyl-$C_1$–$C_4$alkyl; $C_1$–$C_4$alkylcarbonyl-$C_1$–$C_4$alkyl; $C_3$–$C_4$alkenyloxycarbonyl-$C_1$–$C_4$alkyl; $C_3$–$C_4$alkynyloxycarbonyl-$C_1$–$C_4$alkyl; halogen; or cyano; and $R_6$ is hydrogen; $C_1$–$C_4$alkyl; nitro; cyano; halogen; $C_1$–$C_4$alkoxycarbonyl; $C_1$–$C_4$haloalkyl; and n is 0, 1 or 2, and the salts thereof with acids, bases and chelating agents.

The definitions employed in this specification encompass the indicated generic terms as well as the individual meanings of the substituents obtainable by combining subgeneric terms, for example the following individual substituents, without any restriction of the invention being thereby implied.

Alkyl is methyl, ethyl, n-propyl, isopropyl, n-butyl, sec-butyl, isobutyl, tert-butyl.

Halogen is fluoro, chloro, bromo and iodo, preferably fluoro, chloro and bromo.

Alkenyloxy and alkynyloxy are preferably allyloxy and propargyloxy. These unsaturated radicals may be straight chain or branched. Each is attached to the oxygen atom through a saturated carbon atom.

Cycloalkyl is cyclopropyl, cyclobutyl, cyclopentyl and cyclohexyl, preferably cyclopropyl, cyclopentyl and cyclohexyl.

Mono- or di-$C_1$–$C_4$-alkylamino radicals are preferably methylamine, dimethylamine, methylethylamine, diisopropylamine, monoisopropylamine.

The $C_1$–$C_4$alkyl-$S(O)_n$- radicals also comprise the thio ethers (n=0) as well as the corresponding sufinyl and sulfonyl radicals (in which n=1 or 2). The preferred radicals are methylthio, ethylthio, methylsulfinyl, ethylsulfinyl, methylsulfonyl and ethylsulfonyl.

The $C_1$–$C_4$haloalkyl-$S(O)_n$- group denotes the respective haloalkylthio, haloalkylsulfinyl and haloalkylsulfonyl radicals. Especially preferred are difluoromethylthio, difluoromethylsulfinyl, difluoromethylsulfonyl, trifluoromethylthio or chlorofluoromethylthio.

The term "haloalkyl" encompasses the wholly or partially identical or different halogen-substituted alkyl groups in accordance with the scope defined herein. Such groups are, typically, trifluoromethyl, difluoromethyl, 1,1,2,2-tetrafluoroethyl, 2-chloroethyl, pentafluoroethyl, chlorodifluoromethyl, dichloromethyl, chlorofluoromethyl, 1,1-dichloro-2,2,2-trifluoroethyl, 1,1-dichloroethyl, bromomethyl or heptafluoroethyl.

$C_1$–$C_4$Alkoxycarbonyl radicals include, typically, methoxycarbonyl, ethoxycarbonyl as well as the isomeric propoxycarbonyls and butoxycarbonyls.

Alkoxy is methoxy, ethoxy, isopropoxy, n-propoxy, n-butoxy, tert-butoxy, isobutoxy and sec-butoxy.

The phenyl radical may be substituted within the scope defined herein by identical or different substituents. Preferably the phenyl radical is unsubstituted or carries up to three substituents. Individual meanings are, in addition to unsubstituted phenyl, 2-chlorophenyl, 4-chlorophenyl, 2,4-dichlorophenyl, 2-methylphenyl, 4-methylphenyl, 2-trifluoromethylphenyl and 4-trifluoromethylphenyl.

Within the defined scope, haloalkoxy denotes the isomeric radicals which are substituted by one or more identical or different halogens, for example trifluoromethoxy, 2,2,2-trifluoroethoxy, 2,2,3,3,3-pentafluoropropoxy, 1,1,2,2-tetrafluoroethoxy, difluoromethoxy or 2-chloroethoxy.

Alkoxyalkyl radicals typically include: 2-ethoxyethyl, 2-methoxyethyl, 3-methoxypropyl, 2-methoxy-1-methylethyl and methoxymethyl.

Owing to their chemical constitution, the compounds of formula I are able to form numerous salts with acids and bases. The invention also relates to these salts with agrochemically suitable acids and bases. The same applies to complexes and chelating agents.

Compositions to be singled out for special mention are those wherein the active ingredient is a compound of formula Ia

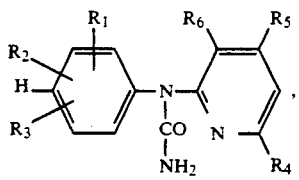

wherein the radicals $R_1$ to $R_6$ are as previously defined, which compound is unsubstituted in 4-position of the phenyl ring.

More particularly, the invention relates to compositions wherein the active ingredient is a compound of formula Ia

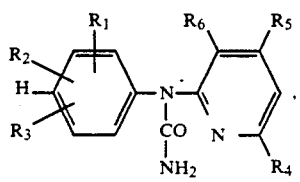

wherein $R_1$, $R_2$ and $R_3$ are each independently of one another hydrogen; nitro; halogen; $C_1$-$C_4$alkyl; $C_1$-$C_4$haloalkyl; $C_1$-$C_4$alkoxy; or $C_1$-$C_4$haloalkoxy;

$R_4$ and $R_5$ are each independently of the other hydrogen; cyano; halogen; $C_1$-$C_4$alkyl; $C_1$-$C_4$alkoxy; $C_1$-$C_4$haloalkyl; $C_1$-$C_4$alkoxy-$C_1$-$C_4$alkyl; phenyl; or furanyl; and $R_6$ is hydrogen; cyano; nitro; halogen; or $C_1$-$C_4$alkoxycarbonyl.

Preferred compositions contain, as active ingredient, a compound of formula Ia

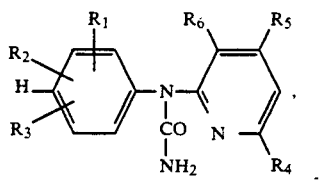

wherein $R_1$ is hydrogen; nitro; halogen; $C_1$-$C_4$haloalkyl; or $C_1$-$C_4$haloalkoxy;

$R_2$ is hydrogen; halogen; or $C_1$-$C_4$alkyl;

$R_3$ is hydrogen; $C_1$-$C_4$alkyl; or halogen;

$R_4$ cyano; halogen; $C_1$-$C_4$alkyl; $C_1$-$C_4$alkoxy; $C_1$-$C_4$haloalkyl; $C_1$-$C_4$alkoxy-$C_1$-$C_4$alkyl; phenyl; or furanyl;

$R_5$ is halogen; $C_1$-$C_4$alkyl; $C_1$-$C_4$haloalkyl; or phenyl; and $R_6$ is hydrogen; cyano; nitro; halogen; or $C_1$-$C_4$alkoxycarbonyl.

To be singled out for special mention are the compositions wherein the active ingredient is a compound of formula Ia

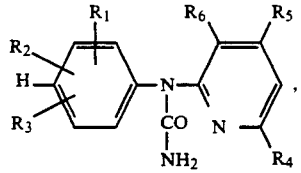

wherein $R_1$ is hydrogen; fluoro; chloro; bromo; iodo; nitro; trifluoromethyl; methoxy; trifluoromethoxy; or difluoromethoxy;

$R_2$ is hydrogen; fluoro; chloro; or methyl;

$R_3$ is hydrogen; chloro; or methyl;

$R_4$ chloro; bromo; $C_1$-$C_4$alkyl; cyano; methoxy; trifluoromethyl; methoxymethyl; phenyl; or furanyl;

$R_5$ is chloro; methyl; trifluoromethyl; chlorodifluoromethyl; difluoromethyl; dichloromethyl; or pentafluoroethyl; and $R_6$ is hydrogen; cyano; nitro; chloro; bromo; or methoxycarbonyl.

Among the above cited compositions which contain a compound of formula Ia as active ingredient, and among the highlighted or preferred compounds of formula Ia, The following isomers of formulae $Ia^1$ to $Ia^6$ merit particular interest:

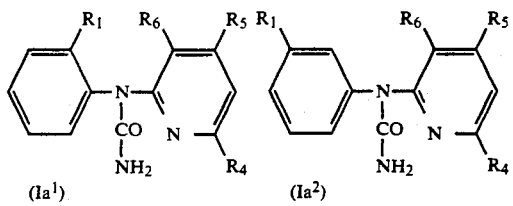

(Ia¹)          (Ia²)

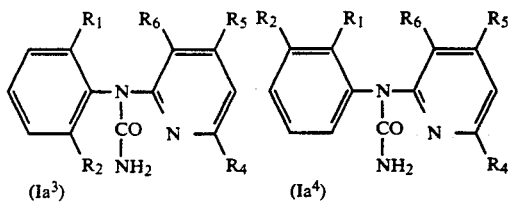

(Ia³)          (Ia⁴)

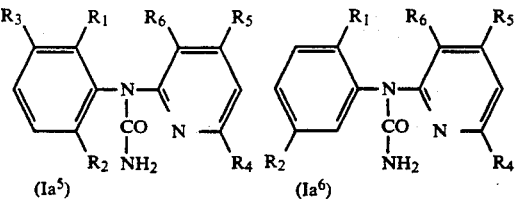

(Ia⁵)          (Ia⁶)

Particularly interesting compositions are also those wherein the active ingredient is a compound of formula Ia, wherein the substituents $R_1$, $R_2$ and $R_3$ are as defined above;

$R_4$ and $R_5$ are each independently of the other $C_1$-$C_4$haloalkyl; or $C_1$-$C_4$alkyl; and $R_6$ is hydrogen.

Further preferred compositions are also those wherein the active ingredient is a compound of formula $Ia^1$ or $Ia^3$, wherein the substituents $R_1$ and $R_2$ are as defined above;

$R_6$ is hydrogen; and $R_4$ and $R_5$ are each independently of the other $C_1$–$C_4$haloalkyl, preferably trifluoromethyl; or $C_1$–$C_4$alkyl.

To be singled out for special mention are also compositions wherein the active ingredient is a compound of formula Ia$^1$ or Ia$^3$, wherein $R_1$ is nitro;
$R_2$ is as defined above; and
$R_4$ and $R_5$ are each independently of the other $C_1$–$C_4$haloalkyl, preferably trifluoromethyl; or $C_1$–$C_4$alkyl.

The invention further relates to the novel ureas of formula I

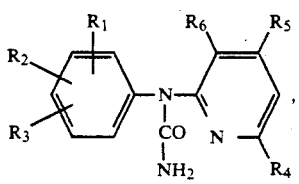

(I)

wherein $R_1$, $R_2$ and $R_3$ are each independently of one another hydrogen; nitro; cyano; halogen; $C_1$–$C_4$alkyl; $C_1$–$C_4$alkyl-S(O)$_n$-; $C_1$–$C_4$alkloxy; $C_1$–$C_4$haloalkyl; $C_1$–$C_4$haloalkoxy; $C_1$–$C_4$haloalkyl-S(O)$_n$-; $C_1$–$C_4$alkoxycarbonyl; $C_1$–$C_4$alkylcarbonyl; carbamoyl; mono-$C_1$–$C_4$alkylcarbamoyl; or di-$C_1$–$C_4$alkylcarbamoyl;

$R_4$ and $R_5$ are each independently of the other hydrogen; $C_1$–$C_4$alkyl; $C_1$–$C_4$alkyl-S(O)$_n$-; $C_1$–$C_4$alkoxy; $C_1$–$C_4$haloalkyl; $C_1$–$C_4$haloalkoxy; $C_1$–$C_4$haloalkyl-S(O)$_n$-; unsubstituted phenyl or phenyl which is substituted by one to three identical or different members of the group consisting of $C_1$–$C_4$alkyl, halogen, $C_1$–$C_4$alkoxy, $C_1$–$C_4$haloalkyl, nitro or cyano; furanyl; thiophenyl; $C_3$–$C_6$cycloalkyl; $C_1$–$C_4$alkoxycarbonyl; $C_1$–$C_4$alkoxy-$C_1$–$C_4$alkyl; $C_1$–$C_4$alkoxycarbonyl-$C_1$–$C_4$alkyl; $C_1$–$C_4$alkylcarbonyl-$C_1$–$C_4$alkyl; $C_3$–$C_4$alkenyloxycarbonyl-$C_1$–$C_4$alkyl; $C_3$–$C_4$alkynyloxycarbonyl-$C_1$–$C_4$alkyl; halogen; or cyano; and $R_6$ is hydrogen; $C_1$–$C_4$alkyl; nitro; cyano; halogen; $C_1$–$C_4$alkoxycarbonyl; $C_1$–$C_4$haloalkyl; and n is 0, 1 or 2, with the proviso that the substituents $R_4$, $R_5$ and $R_6$ may not all simultaneously be hydrogen, and the salts thereof with acids, bases and chelating agents.

To be singled out for special mention are the compounds of formula Ia which are unsubstituted in the 4-position of the phenyl ring

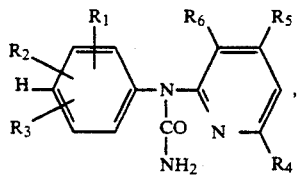

(Ia)

wherein the substituents $R_1$ to $R_6$ are as previously defined.

The invention relates in particular to compounds of formula Ia

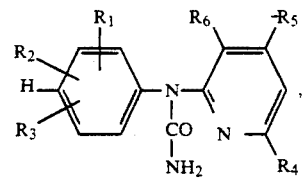

(Ia)

wherein $R_1$, $R_2$ and $R_3$ are each independently of one another hydrogen; nitro; halogen; $C_1$–$C_4$alkyl; $C_1$–$C_4$haloalkyl; $C_1$–$C_4$alkoxy; or $C_1$–$C_4$haloalkoxy;

$R_4$ and $R_5$ are each independently of the other hydrogen; cyano; halogen; $C_1$–$C_4$alkyl; $C_1$–$C_4$alkoxy; $C_1$–$C_4$haloalkyl; $C_1$–$C_4$alkoxy-$C_1$–$C_4$alkyl; phenyl; or furanyl; and $R_6$ is hydrogen; cyano; nitro; halogen; or $C_1$–$C_4$alkoxycarbonyl.

Preferred compounds of formula Ia

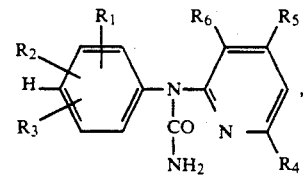

(Ia)

are those wherein $R_1$ is hydrogen; nitro; halogen; $C_1$–$C_4$haloalkyl; or $C_1$–$C_4$haloalkoxy;

$R_2$ is hydrogen; halogen; or $C_1$–$C_4$alkyl;

$R_3$ is hydrogen; $C_1$–$C_4$alkyl; or halogen;

$R_4$ cyano; halogen; $C_1$–$C_4$alkyl; $C_1$–$C_4$alkoxy; $C_1$–$C_4$haloalkyl; $C_1$–$C_4$alkoxy-$C_1$–$C_4$alkyl; phenyl; or furanyl;

$R_5$ is halogen; $C_1$–$C_4$alkyl; $C_1$–$C_4$haloalkyl; or phenyl; and $R_6$ is hydrogen; cyano; nitro; halogen; or $C_1$–$C_4$alkoxycarbonyl.

To be singled out for special mention are the ureas of formula Ia (Ia)

wherein $R_1$ is hydrogen; fluoro; chloro; bromo; iodo; nitro; trifluoromethyl; methoxy; trifluoromethoxy; or difluoromethoxy;

$R_2$ is hydrogen; fluoro; chloro; or methyl;

$R_3$ is hydrogen; chloro; or methyl;

$R_4$ chloro; bromo; $C_1$–$C_4$alkyl; cyano; methoxy; trifluoromethyl; methoxymethyl; phenyl; or furanyl;

$R_5$ is chloro; methyl; trifluoromethyl; chlorodifluoromethyl; difluoromethyl; dichloromethyl; or pentafluoroethyl; and $R_6$ is hydrogen; cyano; nitro; chloro; bromo; or methoxycarbonyl.

Among the above cited compounds of formula Ia, and among the highlighted or preferred compounds of formula Ia, the following isomers of formulae Ia¹ to Ia⁶ merit particular interest:

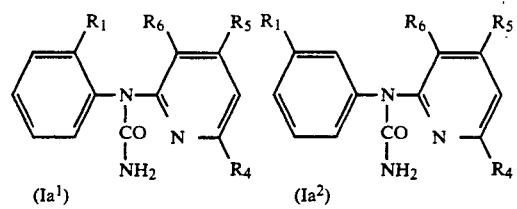
(Ia¹)   (Ia²)

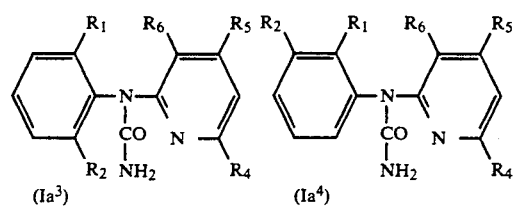
(Ia³)   (Ia⁴)

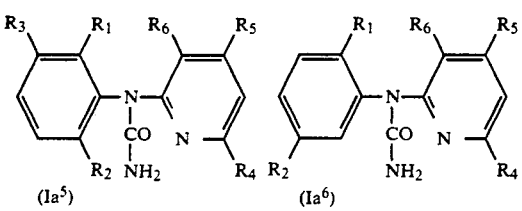
(Ia⁵)   (Ia⁶)

Particularly interesting compounds of formula Ia are also those, wherein
  $R_1$, $R_2$ and $R_3$ are as previously defined;
  $R_4$ and $R_5$ are each independently of the other $C_1$-$C_4$-haloalkyl; or $C_1$-$C_4$alkyl; and
  $R_6$ is hydrogen.

Further preferred compounds are also those the compounds of formula Ia¹ or Ia³, wherein
  $R_1$ and $R_2$ are as previously defined;
  $R_6$ is hydrogen; and
  $R_4$ and $R_5$ are each independently of the other $C_1$-$C_4$-haloalkyl, preferably trifluoromethyl; or $C_1$-$C_4$alkyl.

To be singled out for special mention are also compounds of formula Ia¹ or Ia³, wherein
  $R_1$ is nitro;
  $R_2$ is as defined above; and
  $R_4$ and $R_5$ are each independently of the other $C_1$-$C_4$-haloalkyl, preferably trifluoromethyl; or $C_1$-$C_4$alkyl.

The compounds of formula I can be prepared by
a) phosgenating an aniline of formula II, wherein the substituents $R_1$ to $R_6$ are as defined for formula I, to a carbamyl chloride of formula III and, in a second step, reacting said chloride with $NH_3$ to a urea of formula I

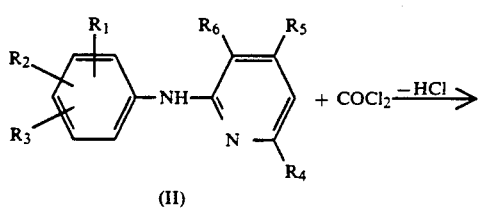
(II)

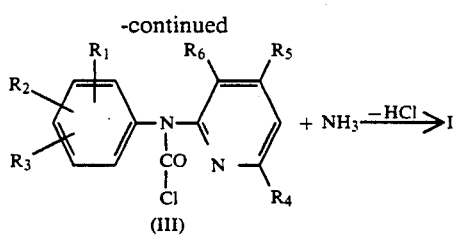
(III)

or b) reacting an aniline of formula II, wherein $R_1$ to $R_6$ are as defined for formula I, with the halosulfonylisocyanate V to a halosulfonylurea of formula IV, and hydrolysing said urea, in a second step or direct, to a compound of formula I, wherein Y is a group which is removable under the reaction conditions, for example a halogen atom such as a chlorine atom:

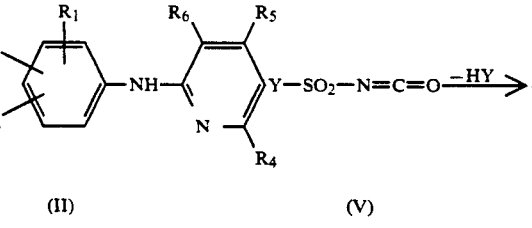
(II)   (V)

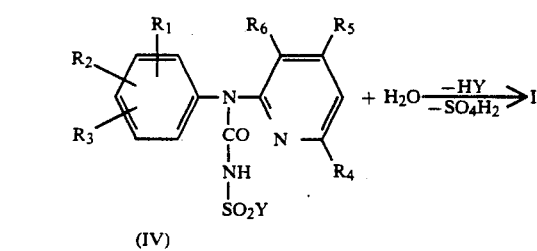
(IV)

It is also possible to prepare ureas of formula I'

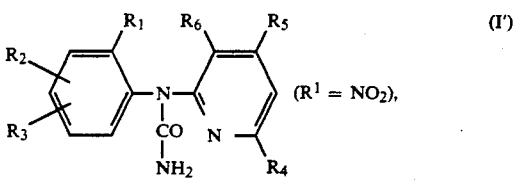
(I')  ($R^1 = NO_2$), wherein $R^1$ is in the ortho-position of the phenyl ring and is nitro, and $R_2$ to $R_6$ are as defined for formula I, by
c) rearranging a sulfonylurea of formula VI by treatment with an aqueous base to a urea of formula I, preferably using NaOH/water or KOH/water as aqueous base:

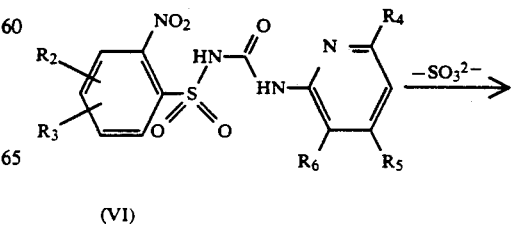
(VI)

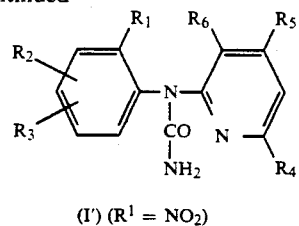

(I') ($R^1 = NO_2$)

The reactions II→III, II→IV and III→I, which proceed with dehydrohalogenation or HY elimination, are preferably carried out using acid acceptors (bases).

Suitable acid acceptors are inorganic bases, for example tertiary amines such as trialkylamines (trimethylamine, triethylamine, tripropylamine and the like), pyridines (pyridine, 4-dimethylaminopyridine, 4-pyrrolidinylaminopyridine and the like), alcoholates such as potassium tert-butylate, sodium methanolate, sodium ethanolate and the like. The base-activated reactions, such as also the reaction VI→I', can also be carried out under phase transfer conditions with bases by procedures which are known per se (Lit. Dehmlow & Dehmlow, Phase Transfer Catalysis; Verlag Chemie, Weinheim, 1983).

The invention further relates to the novel compounds of formula II

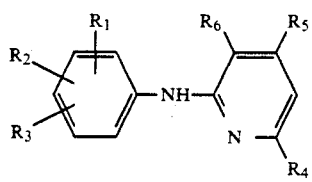

(II)

wherein $R_1$ to $R_6$ are as defined for formula I.

Particularly preferred are the anilines of formula IIa$^1$ or IIa$^3$

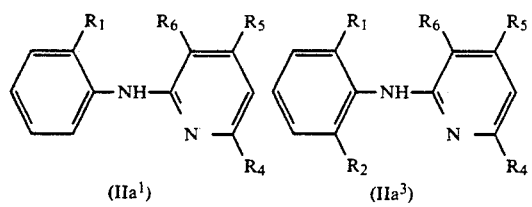

(IIa$^1$)    (IIa$^3$)

Also to be highlighted are the compounds of formula IIa$^1$ or IIa$^3$, wherein $R_1$ and $R_2$ are as previously defined;

$R_6$ is hydrogen; and $R_4$ and $R_5$ are each independently of the other $C_1$-$C_4$-haloalkyl, preferably trifluoromethyl; or $C_1$-$C_4$alkyl.

Further compounds of particular interest are the compounds of formula IIa$^1$ or IIa$^3$, wherein $R_1$ is nitro;

$R_2$ is as previously defined;

$R_4$ and $R_5$ are each independently of the other $C_1$-$C_4$-haloalkyl, preferably trifluoromethyl; or $C_1$-$C_4$alkyl; and $R_6$ is hydrogen.

The compounds of formula II can be prepared a) by reacting an aniline of formula VII, wherein $R_1$ to $R_3$ are as previously defined, with a pyridine of formula III, wherein $R_4$ to $R_6$ are as defined for formula II and X is halogen, $C_1$-$C_4$alkyl-$SO_2$-, or phenyl-$SO_2$-, by treatment with a base

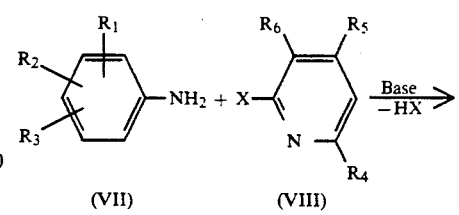

(VII)   (VIII)

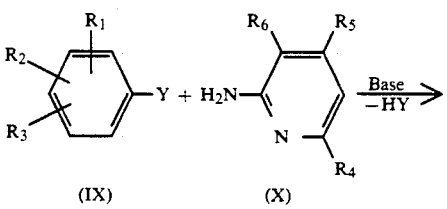

(II)

or b) reacting a halobenzene of formula IX, wherein $R_1$, and $R_2$ and $R_3$ are as defined for formula II and Y is halogen, by treatment with a base, with a 2-aminopyridine of formula X,

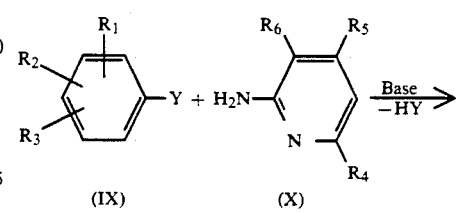

(IX)   (X)

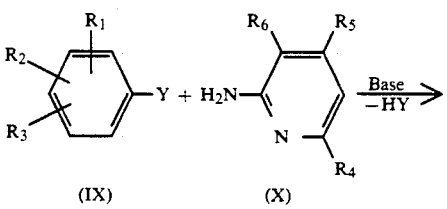

(II)

Suitable bases for the above processes for the preparation of compounds of formula II are alkali metal hydrides such as sodium hydride or potassium hydride, alkyl metal amides such as sodium amide or potassium amide, or organometallic compounds such as butyllithium or phenyllithium.

The invention also relates to the novel carbamyl chlorides of formula III

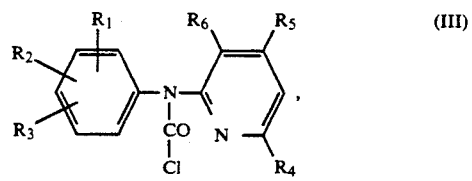

(III)

wherein $R_1$ to $R_6$ are as defined for formula I.

The compounds of formula III can be prepared by phosgenating an aniline of formula II, wherein $R_1$ to $R_6$ are as defined for formula I,

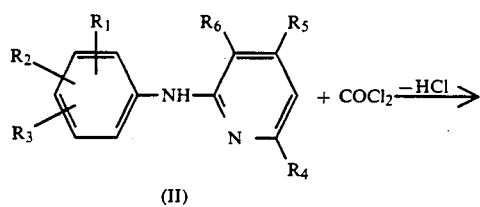

(II)

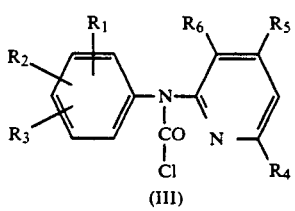

(III)

The invention also relates to the novel halosulfonylureas of formula IV

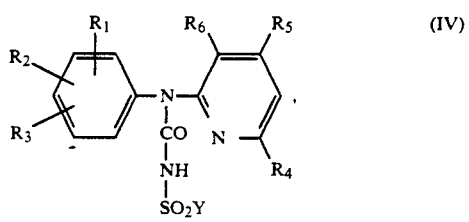

wherein $R_1$ to $R_6$ are as defined for formula I.

The compounds of formula IV can be prepared by reacting an aniline of formula II, wherein $R_1$ to $R_6$ are as defined for formula I, with a halosulfonylisocyanate of formula V, wherein Y is halogen, preferably chloro:

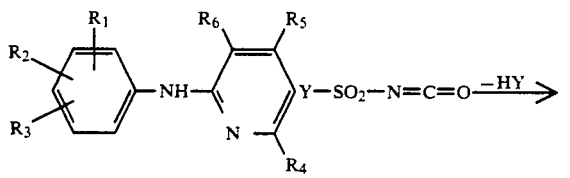

(II)                                                (V)

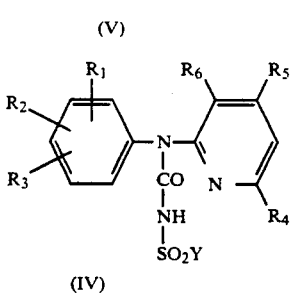

(IV)

The compounds of formula I are highly active herbicides which, when used at appropriate rates of application, are also suitable for use as selective herbicides for controlling weeds in crops of useful plants. Crop plants such as cereals (rye, barley, oats, corn), maize, sorghum, rice, cotton, soybeans, rape and sun flowers suffer almost no damage at low rates of application. At increased rates of application, the growth of the crops plants is only minimally affected. When applied at very high rates of application, the compounds of formula I act as total herbicides.

The selective herbicidal activity of the compounds of this invention is observed in pre- and postemergence application. These compounds can therefore be used with equally successful results pre- and postemergence for selective weed control. However, preemergence application of the compounds of formula I is preferred.

The invention also relates to herbicidal compositions which which contain a novel compound of formula I and to methods of controlling weeds pre- and postemergence.

The compounds of formula I also have plant growth regulating properties. The growth of moncots and dicots is inhibited.

Inhibition of the vegetative growth of many crop plants permits more plants to be sown per crop area, so that a higher yield may be obtained per unit of area.

A further mechanism of yield increase using growth regulators resides in the feature that nutrients are increasingly able to promote flower formation and fruiting whilst the vegetative growth is inhibited. At higher rates of application, weeds and grasses are so severely inhibited in their growth that they wither.

The growth regulators of formula I can be used with particular advantage for regulating the growth of underseeds in maize crops.

Suitable underseeds in maize crops are mainly those plants which cover the soil between the individual maize plants and thus primarily counteract soil erosion in maize crops. Plants suitable as underseeds are, for example, rape, clover, grasses or legumes.

When used in suitable concentrations, the compounds of formula I inhibit the new growth of grasses. This inhibition makes it possible to reduce the number of necessary cuts of areas of grass (parks, gardens and the like) and to increase the intervals between individual cuts. For this purpose, granular formulations of the compounds of formula I may be usd with particular advantage. The granules may contain the compound of formula I by itself, together with conventional adjuvants and carriers, or the compound of formula I may be formulated to a granular composition together with a mineral fertiliser and/or with further optional chemical agents for controlling moss and other undesirable plant growth in areas of grass. The utility as spreading granules makes it possible with the aid of the machines customarily employed for treating areas of grass to apply the granules and thus to inhibit the new growth of grass for an extended period of time. The granular formulation can be prepared in a manner known per se and preferably has a granular size of 0.1 to 2.0 mm, most preferably of 0.25 to 1.0 mm.

The compounds of formula I are ordinarily applied with success at rates of application of 0.005 to 5 kg/ha, preferably 0.1 to 3 kg/ha. The concentration necessary for achieving the desired effect can be determined experimentally. It will depend on the nature of the activity (selective herbicide, total herbicide, growth regulation), on the development stage of the crop plant and of the weed, as well as on the application (place, time, method of application) and, depending on these parameters, can vary within further limits.

The compounds of formula I can also be applied with advantage to the propagation parts of the crop plants. Propagation parts are seeds, cuttings or other parts of plants from which the crop plant can be reared. Seed dressing is to be singled out for special mention in this connection. Propagation parts treated with an effective amount of a compound of formula I also fall within the scope of this invention.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

Thus the compounds of formula I can also be applied to mineral fertilisers (dressing).

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphated adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyl bis(2-chloroethyl)ethylammonium bromide.

The surfactants customarily employed in the art of formulation are described e.g. in the following publications:

"1987 International Mc Cutcheon's Emulsifiers & Detergents", Glen Rock N.J. USA, Dr. Helmut Stache, "Tensid-Taschenbuch" (Handbook of Surfactants), 2nd. ed., C. Hanser Verlag Munich/Vienna 1981, The compositions usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed in particular of the following constituents (% = percentage by weight):

---

Emulsifiable concentrates compound of formula I:       1 to 20%, preferably 5 to 10%

| -continued | |
|---|---|
| surfactant: | 5 to 30%, preferably 10 to 20% |
| liquid carrier: | 50 to 94%, preferably 70 to 85% |
| Dusts | |
| compound of formula I: | 0.1 to 10%, preferably 0.1 to 1% |
| solid carrier: | 99.9 to 90%, preferably 99.9 to 99% |
| Suspension concentrates | |
| compound of formula I: | 5 to 75%, preferably 10 to 50% |
| water: | 94 to 25%, preferably 90 to 30% |
| surfactant: | 1 to 40%, preferably 2 to 30% |
| Wettable powders | |
| compound of formula I: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| compound of formula I: | 0.5 to 30%, preferably 3 to 15% |
| solid carrier: | 99.5 to 70%, preferably 97 to 85%. |
| Spreading granules | |
| compound of formula I: | 0.01 to 30%, preferably 0.05 to 15% |
| tackifier: | 0.05 to 5%, preferably 0.1 bis 2% |
| surfactant: | 0.5 to 20%, preferably 1 to 15% |
| solid carrier: | 99.44 to 45%, preferably 95 bis 65%. |

Whereas commercial formulations are preferably formulated as concentrates, the end user will normally employ dilute formulations. The formulations can be diluted to a concentration as low as 0.001% of active ingredient. The rates of application will normally be from 0.005 to 5 kg of active ingredient per hectare.

The compositions can also contain further ingredients such as antifoams, preservatives, viscosity regulators, binders, tackifiers and fertilisers or other chemical agents to obtain special effects.

PREPARATORY EXAMPLES

P1.
N-(2,6-Dichlorophenyl)-N-(4-trifluoromethyl-6-methylpyridin-2-yl)urea 3.2 g (0.01 mol) of 2-(2,6-dichloroanilino)-4-trifluoromethyl-6-methylpyridine are dissolved in 80 ml of ethyl acetate and the solution is cooled to 0° C. Then 1.8 g (0.013 mol) of chlorosulfonyl isocyanate are added. The reaction mixture is stirred for 2 hours at 0°–5° C. and then 20 ml of ice-water are added. After stirring for 30 minutes, the ethyl acetate phase is separated, washed with brine, dried over sodium sulfate, and concentrated by evaporation. The product crystallises on trituration with hexane.

Crystals of the title compound of formula

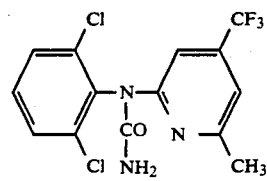

are isolated in a yield of 3 g (83%). Melting point: 165° C. (Compound 1.033).

The compounds of Table 1 can be prepared in a manner analogous to that described in this Example:

TABLE 1

Compounds of formula

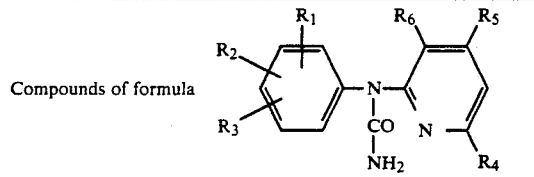

| Comp. No. | R₁ | R₂ | R₃ | R₄ | R₅ | R₆ | Physical data |
|---|---|---|---|---|---|---|---|
| 1.001 | H | H | H | CH₃ | CF₃ | H | m.p. 134° C. |
| 1.002 | H | H | H | CH₃ | CF₃ | CN | |
| 1.003 | H | H | H | CH₃ | CH₃ | CN | |
| 1.004 | 2-Cl | H | H | CH₃ | CH₃ | H | |
| 1.005 | 2-Cl | H | H | CH₃ | CF₃ | H | m.p. 122–123° C. |
| 1.006 | 2-Cl | H | H | CH₃ | Cl | H | |
| 1.007 | 2-Cl | H | H | Cl | CH₃ | H | |
| 1.008 | 2-Br | H | H | CH₃ | CF₃ | H | m.p. 127–128° C. |
| 1.009 | 2-Br | H | H | CF₃ | CH₃ | H | |
| 1.010 | 2-Br | H | H | C₂H₅ | CF₃ | H | |
| 1.011 | 2-Br | H | H | i-C₃H₇ | CF₃ | H | |
| 1.012 | 2-Br | H | H | O—CH₃ | CF₃ | H | |
| 1.013 | 2-Br | H | H | Cl | CF₃ | H | |
| 1.014 | 2-Br | H | H | CH₃ | CH₃ | H | |
| 1.015 | 2-Br | H | H | Cl | CH₃ | H | |
| 1.016 | 2-Br | H | H | CH₃ | CF₃ | CN | |
| 1.017 | 2-CF₃ | H | H | Cl | CH₃ | H | |
| 1.018 | 2-CF₃ | H | H | CH₃ | CF₃ | H | |
| 1.019 | 2-CF₃ | H | H | CF₃ | CH₃ | H | |
| 1.020 | 2-CF₃ | H | H | C₂H₅ | CF₃ | H | |
| 1.021 | 2-OCHF₂ | H | H | CH₃ | CF₃ | CN | |
| 1.022 | 2-OCHF₂ | H | H | CH₃ | CF₃ | H | |
| 1.023 | 2-OCHF₂ | H | H | C₂H₅ | CF₃ | H | |
| 1.024 | 2-I | H | H | CH₃ | CF₃ | H | |
| 1.025 | 2-I | H | H | C₂H₅ | CF₃ | H | |
| 1.026 | 2-F | H | H | CH₃ | CH₃ | H | |
| 1.027 | 2-F | H | H | CH₃ | CF₃ | H | |
| 1.028 | 2-Cl | 3-Cl | H | CH₃ | CF₃ | H | m.p. 125–126° C. |
| 1.029 | 2-Cl | 5-Cl | H | CH₃ | CF₃ | H | m.p. 138° C. (dec.) |
| 1.030 | 2-Cl | 5-Cl | H | CH₃ | CH₃ | H | |
| 1.031 | 2-Cl | 5-Cl | H | Cl | CH₃ | H | |
| 1.032 | 2-Cl | 6-Cl | H | CH₃ | CH₃ | H | |

TABLE 1-continued

Compounds of formula

| Comp. No. | $R_1$ | $R_2$ | $R_3$ | $R_4$ | $R_5$ | $R_6$ | Physical data |
|---|---|---|---|---|---|---|---|
| 1.033 | 2-Cl | 6-Cl | H | $CH_3$ | $CF_3$ | H | m.p. 165° C. (dec.) |
| 1.034 | 2-Cl | 6-Cl | H | $CF_3$ | $CH_3$ | H | |
| 1.035 | 2-Cl | 6-Cl | H | $CH_3$ | $CF_3$ | CN | |
| 1.036 | 2-Cl | 6-Cl | H | $CH_3$ | $CF_3$ | $NO_2$ | |
| 1.037 | 2-Cl | 6-Cl | H | $CH_3$ | $CF_3$ | H | |
| 1.038 | 2-Cl | 6-Cl | H | Phenyl | $CF_3$ | H | |
| 1.039 | 2-Cl | 6-Cl | H | 2-Furyl | $CF_3$ | H | |
| 1.040 | 2-Cl | 6-Cl | H | $C_2H_5$ | $CF_3$ | H | |
| 1.041 | 2-Cl | 6-Cl | H | n-$C_3H_7$ | $CF_3$ | H | |
| 1.042 | 2-Cl | 6-Cl | H | i-$C_3H_7$ | $CF_3$ | H | |
| 1.043 | 2-Cl | 6-Cl | H | $CH_3$ | phenyl | H | |
| 1.044 | 2-Cl | 6-Cl | H | $CF_3$ | H | H | |
| 1.045 | 2-Cl | 6-Cl | H | H | $CF_3$ | H | |
| 1.046 | 2-Cl | 6-Cl | H | $CH_2OCH_3$ | $CF_3$ | H | |
| 1.047 | 2-Cl | 6-Cl | H | $CH_3$ | $CF_2Cl$ | H | m.p. 157–158° C. |
| 1.048 | 2-Cl | 6-Cl | H | $C_2H_5$ | $CF_2Cl$ | H | |
| 1.049 | 2-Cl | 6-Cl | H | $CH_3$ | $CHF_2$ | H | |
| 1.050 | 2-Cl | 6-Cl | H | $CH_3$ | $CHCl_2$ | H | |
| 1.051 | 2-Cl | 6-Cl | H | $CH_3$ | Cl | $CH_3$ | |
| 1.052 | 2-Cl | 6-Cl | H | Cl | $CH_3$ | H | |
| 1.053 | 2-Cl | 6-$CH_3$ | H | $CH_3$ | $CF_3$ | CN | |
| 1.054 | 2-Cl | 6-$CH_3$ | H | $CH_3$ | $CF_3$ | H | m.p. 148° C. |
| 1.055 | 2-Cl | 6-$CH_3$ | H | $C_2H_5$ | $CF_3$ | H | |
| 1.056 | 2-Cl | 6-$CH_3$ | H | i-$C_3H_7$ | $CF_3$ | H | |
| 1.057 | 2-Cl | 6-$CH_3$ | H | $CH_3$ | $CF_2Cl$ | H | m.p. 166–167° C. |
| 1.058 | 2-Cl | 6-$CH_3$ | H | $CH_3$ | $CHF_2$ | H | |
| 1.059 | 2-Cl | 6-$CH_3$ | H | $C_2H_5$ | $CF_2Cl$ | H | |
| 1.060 | 2-Cl | 6-F | H | $CH_3$ | $CF_3$ | H | |
| 1.061 | 2-Cl | 6-F | H | $C_2H_5$ | $CF_3$ | H | |
| 1.062 | 2-Cl | 6-F | H | i-$C_3H_7$ | $CF_3$ | H | |
| 1.063 | 2-Cl | 6-F | H | $CH_3$ | $CH_3$ | H | |
| 1.064 | 2-Cl | 6-Cl | 3-$CH_3$ | $CH_3$ | $CF_3$ | H | |
| 1.065 | 2-Cl | 6-Cl | 3-$CH_3$ | $C_2H_5$ | $CF_3$ | H | |
| 1.066 | 2-Cl | 6-Cl | 3-$CH_3$ | $CF_3$ | $CH_3$ | H | |
| 1.067 | 2-Cl | 6-Cl | 3-Cl | $CH_3$ | $CF_3$ | H | |
| 1.068 | 2-Cl | 6-Cl | 3-Cl | Cl | $CH_3$ | H | |
| 1.069 | 2-Cl | 5-F | H | $CH_3$ | $CF_3$ | H | |
| 1.070 | 2-Cl | 5-F | H | $C_2H_5$ | $CF_3$ | H | |
| 1.071 | 2-F | 5-F | H | $CH_3$ | Cl | H | |
| 1.072 | 2-F | 5-F | H | $CH_3$ | $CF_3$ | H | m.p. 109° C. |
| 1.073 | 2-F | 5-F | H | $CF_3$ | $CH_3$ | H | |
| 1.074 | 2-F | 5-F | H | $C_2H_5$ | $CF_3$ | H | |
| 1.075 | 2-F | 5-F | H | i-$C_3H_7$ | $CF_3$ | H | |
| 1.076 | 2-F | 5-F | H | $CH_3$ | $CF_2Cl$ | H | |
| 1.077 | 2-F | 5-F | H | $CH_3$ | $CHF_2$ | H | |
| 1.078 | 2-F | 5-F | H | $CH_3$ | $C_2F_5$ | H | |
| 1.079 | 2-F | 6-F | H | $CH_3$ | $CF_3$ | H | m.p. 153° C. |
| 1.080 | 2-F | 6-F | H | $CF_3$ | $CH_3$ | H | |
| 1.081 | 2-F | 6-F | H | $C_2H_5$ | $CF_3$ | H | |
| 1.082 | 2-$NO_2$ | H | H | $CH_3$ | $CF_3$ | H | m.p. 132-3° (dec.) |
| 1.083 | 2-$NO_2$ | H | H | $C_2H_5$ | $CF_3$ | H | m.p. 114° C. |
| 1.084 | 2-$NO_2$ | H | H | i-$C_3H_7$ | $CF_3$ | H | m.p. 119° C. |
| 1.085 | 2-$NO_2$ | H | H | n-$C_3H_7$ | $CF_3$ | H | m.p. 116° C. |
| 1.086 | 2-$NO_2$ | H | H | i-$C_4H_9$ | $CF_3$ | H | |
| 1.087 | 2-$NO_2$ | H | H | s-$C_4H_9$ | $CF_3$ | H | |
| 1.088 | 2-$NO_2$ | H | H | t-$C_4H_9$ | $CF_3$ | H | |
| 1.089 | 2-$NO_2$ | H | H | n-$C_4H_9$ | $CF_3$ | H | |
| 1.090 | 2-$NO_2$ | H | H | $CH_3$ | $C_2F_5$ | H | |
| 1.091 | 2-$NO_2$ | H | H | $C_2H_5$ | $C_2F_5$ | H | |
| 1.092 | 2-$NO_2$ | H | H | $CH_3$ | $CF_2Cl$ | H | m.p. 141–142° C. |
| 1.093 | 2-$NO_2$ | H | H | $C_2H_5$ | $CF_2Cl$ | H | |
| 1.094 | 2-$NO_2$ | H | H | $CH_3$ | $CHF_2$ | H | m.p. 149° C. |
| 1.095 | 2-$NO_2$ | H | H | $C_2H_5$ | $CHF_2$ | H | |
| 1.096 | 2-$NO_2$ | H | H | $CH_3$ | $CHCl_2$ | H | |
| 1.097 | 2-$NO_2$ | H | H | $C_2H_5$ | $CHCl_2$ | H | |
| 1.098 | 2-$NO_2$ | H | H | $CH_2OCH_3$ | $CF_3$ | H | |
| 1.099 | 2-$NO_2$ | H | H | $CF_3$ | $CH_3$ | H | m.p. 160° C. |
| 1.100 | 2-$NO_2$ | H | H | $CF_3$ | H | H | m.p. 74–76° C. |
| 1.101 | 2-$NO_2$ | H | H | H | $CF_3$ | H | m.p. 135° C. |
| 1.102 | 2-$NO_2$ | H | H | $CH_3$ | $CH_3$ | H | m.p. 154° C. |
| 1.103 | 2-$NO_2$ | H | H | $CH_3$ | $CF_3$ | CN | |

TABLE 1-continued

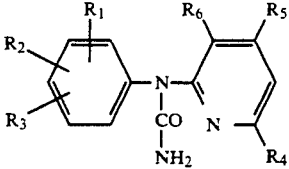

Compounds of formula

| Comp. No. | $R_1$ | $R_2$ | $R_3$ | $R_4$ | $R_5$ | $R_6$ | Physical data |
|---|---|---|---|---|---|---|---|
| 1.104 | 2-$NO_2$ | H | H | $CH_3$ | $CF_3$ | $NO_2$ | |
| 1.105 | 2-$NO_2$ | H | H | $CH_3$ | $CF_3$ | Cl | |
| 1.106 | 2-$NO_2$ | H | H | $C_2H_5$ | $CF_3$ | CN | |
| 1.107 | 2-$NO_2$ | H | H | $CH_3$ | $CF_3$ | $COOCH_3$ | |
| 1.108 | 2-$NO_2$ | H | H | O—$CH_3$ | $CF_3$ | H | |
| 1.109 | 2-$NO_2$ | H | H | O—$CH_3$ | $CH_3$ | H | |
| 1.110 | 2-$NO_2$ | H | H | CN | $CH_3$ | H | |
| 1.111 | 2-$NO_2$ | H | H | Cl | $CH_3$ | H | m.p. 185° C. |
| 1.112 | 2-$NO_2$ | H | H | $CH_3$ | Cl | H | m.p. 146° C. |
| 1.113 | 2-$NO_2$ | 6-F | H | $CH_3$ | $CF_3$ | H | m.p. 140° C. |
| 1.114 | 2-$NO_2$ | 6-F | H | $C_2H_5$ | $CF_3$ | H | |
| 1.115 | 2-$NO_2$ | 6-F | H | $CF_3$ | $CH_3$ | H | |
| 1.116 | 2-$NO_2$ | 6-F | H | Cl | $CH_3$ | H | |
| 1.117 | 2-$NO_2$ | 6-F | H | $CH_3$ | $CH_3$ | H | |
| 1.118 | 2-$NO_2$ | 6-Cl | H | $CH_3$ | $CF_3$ | H | |
| 1.119 | 2-$NO_2$ | 6-Cl | H | $C_2H_5$ | $CF_3$ | H | |
| 1.120 | 2-$NO_2$ | 6-Cl | H | $CH_3$ | $CF_3$ | CN | |
| 1.121 | 2-$NO_2$ | 6-Cl | H | $CF_3$ | $CH_3$ | H | |
| 1.122 | 2-$NO_2$ | 6-$CH_3$ | H | $CH_3$ | $CF_3$ | H | m.p. 174° C. |
| 1.123 | 2-$NO_2$ | 6-$CH_3$ | H | $C_2H_5$ | $CF_3$ | H | m.p. 142–143° C. |
| 1.124 | 2-$NO_2$ | 6-$CH_3$ | H | i-$C_3H_7$ | $CF_3$ | H | |
| 1.125 | 2-$NO_2$ | 6-$CH_3$ | H | i-$C_4H_9$ | $CF_3$ | H | |
| 1.126 | 2-$NO_2$ | 6-$CH_3$ | H | $CH_3$ | $CF_2Cl$ | H | m.p. 152–155° C. |
| 1.127 | 2-$NO_2$ | 6-$CH_3$ | H | $C_2H_5$ | $CF_2Cl$ | H | |
| 1.128 | 2-$NO_2$ | 6-$CH_3$ | H | i-$C_3H_7$ | $CF_2Cl$ | H | |
| 1.129 | 2-$NO_2$ | 6-$CH_3$ | H | i-$C_4H_9$ | $CF_2Cl$ | H | |
| 1.130 | 2-$NO_2$ | 6-$CH_3$ | H | $CH_3$ | $CHF_2$ | H | m.p. 168° C. |
| 1.131 | 2-$NO_2$ | 6-$CH_3$ | H | $C_2H_5$ | $CHF_2$ | H | |
| 1.132 | 2-$NO_2$ | 6-$CH_3$ | H | i-$C_3H_7$ | $CHF_2$ | H | |
| 1.133 | 2-$NO_2$ | 6-$CH_3$ | H | i-$C_4H_9$ | $CHF_2$ | H | |
| 1.134 | 2-$NO_2$ | 6-$CH_3$ | H | $CH_3$ | $CHCl_2$ | H | |
| 1.135 | 2-$NO_2$ | 6-$CH_3$ | H | $C_2H_5$ | $CHCl_2$ | H | |
| 1.136 | 2-$NO_2$ | 6-$CH_3$ | H | i-$C_3H_7$ | $CHCl_2$ | H | |
| 1.137 | 2-$NO_2$ | 6-$CH_3$ | H | i-$C_4H_9$ | $CHCl_2$ | H | |
| 1.138 | 2-$NO_2$ | 6-$CH_3$ | H | $CF_3$ | $CH_3$ | H | |
| 1.139 | 2-$NO_2$ | 6-$CH_3$ | H | $CH_3$ | $CH_3$ | H | |
| 1.140 | 2-$NO_2$ | 6-$CH_3$ | H | Phenyl | $CH_3$ | H | |
| 1.141 | 2-$NO_2$ | 6-$CH_3$ | H | Phenyl | $CF_3$ | H | |
| 1.142 | 2-$NO_2$ | 6-$CH_3$ | H | $CH_3$ | $CF_3$ | CN | |
| 1.143 | 2-$NO_2$ | 6-$CH_3$ | H | $CH_3$ | $CF_3$ | $COOCH_3$ | |
| 1.144 | 2-$NO_2$ | 6-$CH_3$ | H | $CH_3$ | $CF_3$ | Cl | |
| 1.145 | 2-$NO_2$ | 6-$CH_3$ | H | $CH_3$ | $CF_3$ | Br | |
| 1.146 | 2-$NO_2$ | 6-$CH_3$ | H | $CH_3$ | Cl | $CH_3$ | |
| 1.147 | 2-$NO_2$ | 6-$CH_3$ | H | $CH_3$ | $CF_3$ | $NO_2$ | |
| 1.148 | 2-$NO_2$ | 6-$CH_3$ | H | Cl | $CF_3$ | H | |
| 1.149 | 2-$NO_2$ | 6-$CH_3$ | H | Br | $CF_3$ | H | |
| 1.150 | 2-$NO_2$ | 6-$CH_3$ | H | O—$CH_3$ | $CF_3$ | H | |
| 1.151 | 2-$NO_2$ | 5-F | H | $CH_3$ | $CF_3$ | H | m.p. 134° C. |
| 1.152 | 2-$NO_2$ | 5-F | H | $CH_3$ | $CF_3$ | CN | |
| 1.153 | 2-$NO_2$ | 5-F | H | $C_2H_5$ | $CF_3$ | H | |
| 1.154 | 2-$NO_2$ | 5-F | H | $CF_3$ | $CF_3$ | H | |
| 1.155 | 2-$NO_2$ | 5-F | H | $CH_3$ | $CH_3$ | H | |
| 1.156 | 2-$NO_2$ | 5-F | H | $C_2H_5$ | $CH_3$ | H | |
| 1.157 | 2-$NO_2$ | 5-F | H | $CF_3$ | $CH_3$ | H | |
| 1.158 | 2-$NO_2$ | 5-F | H | Cl | $CF_3$ | H | |
| 1.159 | 2-$NO_2$ | 5-F | H | Cl | $CH_3$ | H | |
| 1.160 | 2-$OCF_3$ | H | H | $CF_3$ | $CH_3$ | H | |
| 1.161 | 2-$OCF_3$ | H | H | $CH_3$ | $CF_3$ | H | |
| 1.162 | 2-CN | H | H | $CH_3$ | $CF_3$ | H | |
| 1.163 | 2-CN | H | H | $C_2H_5$ | $CF_3$ | H | |
| 1.164 | 2-$NO_2$ | 5-Cl | H | $CH_3$ | $CF_3$ | H | |
| 1.165 | 2-$NO_2$ | 5-Cl | H | $CF_3$ | $CH_3$ | H | |
| 1.166 | 2-$NO_2$ | 5-$CH_3$ | H | $CH_3$ | $CF_3$ | H | |
| 1.167 | 3-Cl | 5-Cl | H | $CH_3$ | $CF_3$ | H | m.p. 142° C. |
| 1.168 | 3-Cl | 5-Cl | H | $CH_3$ | $CH_3$ | H | |
| 1.169 | 3-F | H | H | $CH_3$ | $CF_3$ | H | |
| 1.170 | 3-F | H | H | $CF_3$ | $CH_3$ | H | |
| 1.171 | 3-F | H | H | $CH_3$ | $CF_3$ | CN | |
| 1.172 | 3-F | H | H | $CH_3$ | $CH_3$ | H | |
| 1.173 | 3-F | H | H | $CH_3$ | $CH_3$ | CN | |
| 1.174 | 3-Cl | H | H | $CH_3$ | $CF_3$ | H | |
| 1.175 | 3-$CF_3$ | H | H | $CH_3$ | $CF_3$ | H | |

TABLE 1-continued

Compounds of formula $$\text{R}_2 \underset{\text{R}_3}{\overset{\text{R}_1}{\bigvee}} - \text{N}(\text{CONH}_2) - \underset{\text{R}_4}{\overset{\text{R}_6 \quad \text{R}_5}{\bigvee}} \text{N}$$

| Comp. No. | $R_1$ | $R_2$ | $R_3$ | $R_4$ | $R_5$ | $R_6$ | Physical data |
|---|---|---|---|---|---|---|---|
| 1.176 | 3-F | 5-F | H | $CH_3$ | $CF_3$ | H | |
| 1.177 | 2-$NO_2$ | H | H | $CF_3$ | $CF_3$ | H | m.p. 169° C. (dec.) |
| 1.178 | 2-$OCH_3$ | H | H | $CH_3$ | $CF_3$ | H | m.p. 141° C. |
| 1.179 | 2-$NO_2$ | H | H | Cl | $CF_3$ | H | m.p. 172° C. |
| 1.180 | H | H | H | Cl | $CF_3$ | H | m.p. 115–116° C. |
| 1.181 | 2-Cl | 6-Cl | H | Cl | $CF_3$ | H | m.p. 179° C. |
| 1.182 | 2-$NO_2$ | 6-$CH_3$ | H | Cl | $CF_3$ | H | m.p. 188° C. |
| 1.183 | 2-Cl | H | H | $CH_3$ | $CF_2Cl$ | H | m.p. 132–135° C. |
| 1.184 | 2-Cl | H | H | $C_2H_5$ | $CF_2Cl$ | H | |
| 1.185 | 2-Cl | H | H | $CH_3$ | $C_2H$ | $H_5$ | |
| 1.186 | 2-Br | H | H | $CH_3$ | $CF_2Cl$ | H | m.p. 137–138° C. |
| 1.187 | 2-Br | H | H | $C_2H_5$ | $CF_2Cl$ | H | |
| 1.188 | 2-Br | H | H | $CH_3$ | $CHF_2$ | H | |
| 1.189 | 2-Br | H | H | $CH_3$ | $C_2F_5$ | H | |
| 1.190 | 2-$CF_3$ | H | H | $CH_3$ | $CF_2Cl$ | H | m.p. 131–132° C. |
| 1.191 | 2-$CF_3$ | H | H | $CH_3$ | $CHF_2$ | H | |
| 1.192 | 2-Cl | 6-Cl | H | $OCH_3$ | $CF_3$ | H | m.p. 182–183° C. |
| 1.193 | 2-Cl | 6-Cl | H | $C_3H_7(i)$ | $CF_2Cl$ | H | |
| 1.194 | 2-Cl | 6-Cl | H | $CH_3$ | $C_2F_5$ | H | |
| 1.195 | 2-Cl | 6-Cl | H | $CH_3$ | $CFCl_2$ | H | |
| 1.196 | 2-Cl | 5-Cl | H | $CH_3$ | $CF_2Cl$ | H | m.p. 128–129° C. |
| 1.197 | 2-Cl | 5-Cl | H | $C_2H_5$ | $CF_2Cl$ | H | |
| 1.198 | 2-$OCHF_2$ | 6-$CH_3$ | H | $CH_3$ | $CF_3$ | H | m.p. 145° C. |
| 1.199 | 2-$OCHF_2$ | 6-$CH_3$ | H | $CH_3$ | $CF_2Cl$ | H | m.p. 124–125° C. |
| 1.200 | 2-$OCHF_2$ | 6-$CH_3$ | H | $C_2H_5$ | $CF_2Cl$ | H | |
| 1.201 | 2-$OCHF_2$ | 6-$CH_3$ | H | $C_3H_7(i)$ | $CF_2Cl$ | H | |
| 1.202 | 2-$OCHF_2$ | 6-$CH_3$ | H | $CH_3$ | $CHF_2$ | H | |
| 1.203 | 2-$OCHF_2$ | 6-$CH_3$ | H | $CH_3$ | $C_2F_5$ | H | |
| 1.204 | 2-$OCHF_2$ | 6-$CH_3$ | H | $C_2H_5$ | $CF_3$ | H | |
| 1.205 | 2-$OCHF_2$ | 6-$CH_3$ | H | $C_3H_7(i)$ | $CF_3$ | H | |
| 1.206 | 2-$NO_2$ | H | H | F | $CH_3$ | H | |
| 1.207 | 2-$NO_2$ | H | H | $CF_3$ | H | $CF_3$ | |
| 1.208 | 2-$NO_2$ | H | H | $CH_3$ | $CH_3$ | CN | m.p. 200–201° C. |
| 1.209 | 2-$NO_2$ | H | H | $CH_3$ | $CH_3$ | H | m.p. 172–173° C. |
| 1.210 | 2-$NO_2$ | H | H | $CF_3$ | H | CN | |
| 1.211 | 2-$NO_2$ | H | H | $C_3H_7(i)$ | $CF_2Cl$ | H | |
| 1.212 | 2-$NO_2$ | H | H | $CH_3$ | $CFCl_2$ | H | |
| 1.213 | 2-$NO_2$ | H | H | $C_2H_5$ | $CFCl_2$ | H | |
| 1.214 | 2-$NO_2$ | 6-F | H | $CH_3$ | $CF_2Cl$ | H | m.p. 145–146° C. |
| 1.215 | 2-$NO_2$ | 6-F | H | $C_2H_5$ | $CF_2Cl$ | H | |
| 1.216 | 2-$NO_2$ | 6-F | H | $C_3H_7(i)$ | $CF_2Cl$ | H | |
| 1.217 | 2-$NO_2$ | 6-F | H | $CH_3$ | $C_2F_5$ | H | |
| 1.218 | 2-$NO_2$ | 6-F | H | $C_2H_5$ | $C_2H_5$ | H | |
| 1.219 | 2-$NO_2$ | 6-F | H | $CH_3$ | $CHF_2$ | H | |
| 1.220 | 2-$NO_2$ | 6-F | H | $C_2H_5$ | $CHF_2$ | H | |
| 1.221 | 2-$NO_2$ | 6-F | H | $CH_3$ | $CFCl_2$ | H | |
| 1.222 | 2-$NO_2$ | 6-Cl | H | $CH_3$ | $CF_2Cl$ | H | |
| 1.223 | 2-$NO_2$ | 6-Cl | H | $C_2H_5$ | $CF_2Cl$ | H | |
| 1.224 | 2-$NO_2$ | 6-$CH_3$ | H | $CH_3$ | $CFCl_2$ | H | |
| 1.225 | 2-$NO_2$ | 6-$CH_3$ | H | $CH_3$ | $C_2F_5$ | H | |
| 1.226 | 2-$NO_2$ | 6-$CH_3$ | H | $C_2H_5$ | $C_2F_5$ | H | |
| 1.227 | 2-$NO_2$ | 5-Cl | H | $CH_3$ | $CF_2Cl$ | H | |
| 1.228 | 2-$NO_2$ | 5-Cl | H | $C_2H_5$ | $CF_2Cl$ | H | |
| 1.229 | 2-$NO_2$ | 5-Cl | H | $CH_3$ | $CHF_2$ | H | |
| 1.230 | 2-$NO_2$ | H | H | $CH_3$ | CN | H | m.p. 172–173° C. |
| 1.231 | 2-$NO_2$ | 6-$C_2H_5$ | H | $CH_3$ | $CF_3$ | H | |
| 1.232 | 2-$NO_2$ | 6-$C_2H_5$ | H | $CH_3$ | $CF_2Cl$ | H | |
| 1.233 | 2-$NO_2$ | 6-$C_2H_5$ | H | $C_2H_5$ | $CF_3$ | H | |

P2. PREPARATION OF THE INTERMEDIATES

P2.1.

2-(2,6-Dichloroanilino-4-trifluoromethyl-6-methylpyridine 4.0 g (0.025 mol) of 2,6-dichloroaniline in 20 ml of dimethyl sulfoxide are added dropwise at 15°–20° C. to 1.2 g (0.05 mol) of sodium hydride in 20 ml of dimethyl sulfoxide. After hydrogen has ceased to evolve, 4.5 g (0.025 mol) of 2-fluoro-4-trifluoromethyl-6-methylpyridine in 10 ml of dimethyl sulfoxide are added dropwise, whereupon the temperature rises to 30° C. The reaction mixture is stirred for 2 hours at room temperature and then ice-water is added. After extraction with diethyl ether, the ether phase is dried over sodium sulfate and concentrated by evaporation. The residue is chromatographed over silica gel with ethyl acetate/hexane (1:3), affording 4.4 g (54.8%) of the title compound of formula

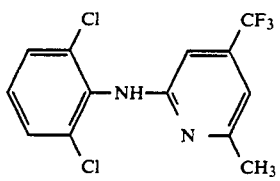

in the form of crystals which melt at 108° C. (compound 2.033).

P.2.2 2-(2-Nitroanilino)-4-methyl-6-chloropyridine 4.3 g (0.03 mol) of 2-amino-4-methyl-6-chloropyridine in 50 ml of dimethyl sulfoxide are added dropwise at 20° C. to a suspension of 1.4 g (0.06 mol) of sodium hydride in 20 ml of dimethyl sulfoxide. After stirring for 1 hour, 4.2 g (0.03 mol) of 2-fluoronitrobenzene in 10 ml of dimethyl sulfoxide are added dropwise, whereupon the temperature rises to 30° C. The reaction mixture is stirred for 2 hours at room temperature and, after addition of ice-water, extracted with ethyl acetate. The extract is dried over sodium sulfate and concentrated by evaporation. The residue is chromatographed over silica gel with ethyl acetate/hexane (1:3), affording 5.0 g of the title compound of formula

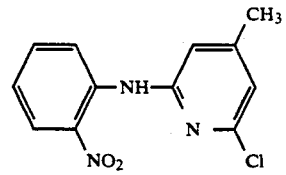

in the form of crystals which melt at 122° C. (compound 2.111).

The compounds of formula II listed in Table 2 can be prepared in analogous manner:

TABLE 2

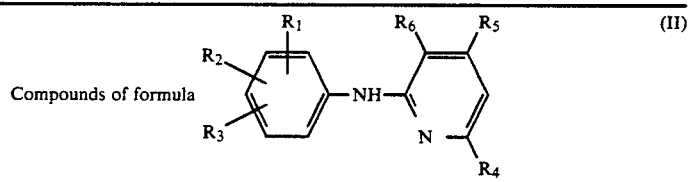

Compounds of formula (II)

| Comp. No. | $R_1$ | $R_2$ | $R_3$ | $R_4$ | $R_5$ | $R_6$ | Physical data |
|---|---|---|---|---|---|---|---|
| 2.001 | H | H | H | $CH_3$ | $CF_3$ | H | $n_D^{25}$ 1.5580 |
| 2.002 | H | H | H | $CH_3$ | $CF_3$ | CN | |
| 2.003 | H | H | H | $CH_3$ | $CH_3$ | CN | |
| 2.004 | 2-Cl | H | H | $CH_3$ | $CH_3$ | H | |
| 2.005 | 2-Cl | H | H | $CH_3$ | $CF_3$ | H | m.p. 53–55° C. |
| 2.006 | 2-Cl | H | H | $CH_3$ | Cl | H | |
| 2.007 | 2-Cl | H | H | Cl | $CH_3$ | H | |
| 2.008 | 2-Br | H | H | $CH_3$ | $CF_3$ | H | m.p. 65–67° C. |
| 2.009 | 2-Br | H | H | $CF_3$ | $CH_3$ | H | |
| 2.010 | 2-Br | H | H | $C_2H_5$ | $CF_3$ | H | |
| 2.011 | 2-Br | H | H | i-$C_3H_7$ | $CF_3$ | H | |
| 2.012 | 2-Br | H | H | O—$CH_3$ | $CF_3$ | H | |
| 2.013 | 2-Br | H | H | Cl | $CF_3$ | H | |
| 2.014 | 2-Br | H | H | $CH_3$ | $CH_3$ | H | |
| 2.015 | 2-Br | H | H | Cl | $CH_3$ | H | |
| 2.016 | 2-Br | H | H | $CH_3$ | $CF_3$ | CN | |
| 2.017 | 2-$CF_3$ | H | H | Cl | $CH_3$ | H | |
| 2.018 | 2-$CF_3$ | H | H | $CH_3$ | $CF_3$ | H | |
| 2.019 | 2-$CF_3$ | H | H | $CF_3$ | $CH_3$ | H | |
| 2.020 | 2-$CF_3$ | H | H | $C_2H_5$ | $CF_3$ | H | |
| 2.021 | 2-$OCHF_2$ | H | H | $CH_3$ | $CF_3$ | CN | |
| 2.022 | 2-$OCHF_2$ | H | H | $CH_3$ | $CF_3$ | H | |
| 2.023 | 2-$OCHF_2$ | H | H | $C_2H_5$ | $CF_3$ | H | |
| 2.024 | 2-I | H | H | $CH_3$ | $CF_3$ | H | |
| 2.025 | 2-I | H | H | $C_2H_5$ | $CF_3$ | H | |
| 2.026 | 2-F | H | H | $CH_3$ | $CH_3$ | H | |
| 2.027 | 2-F | H | H | $CH_3$ | $CF_3$ | H | |
| 2.028 | 2-Cl | 3-Cl | H | $CH_3$ | $CF_3$ | H | m.p. 91–92° C. |
| 2.029 | 2-Cl | 5-Cl | H | $CH_3$ | $CF_3$ | H | m.p. 93° C. |
| 2.030 | 2-Cl | 5-Cl | H | $CH_3$ | $CH_3$ | H | |
| 2.031 | 2-Cl | 5-Cl | H | Cl | $CH_3$ | H | |
| 2.032 | 2-Cl | 6-Cl | H | $CH_3$ | $CH_3$ | H | |
| 2.033 | 2-Cl | 6-Cl | H | $CH_3$ | $CF_3$ | H | Fp. 108° C. |
| 2.034 | 2-Cl | 6-Cl | H | $CF_3$ | $CH_3$ | H | |
| 2.035 | 2-Cl | 6-Cl | H | $CH_3$ | $CF_3$ | CN | |
| 2.036 | 2-Cl | 6-Cl | H | $CH_3$ | $CF_3$ | $NO_2$ | |
| 2.037 | 2-Cl | 6-Cl | H | $CH_3$ | $CF_3$ | H | |
| 2.038 | 2-Cl | 6-Cl | H | phenyl | $CF_3$ | H | |
| 2.039 | 2-Cl | 6-Cl | H | 2-furyl | $CF_3$ | H | |
| 2.040 | 2-Cl | 6-Cl | H | $C_2H_5$ | $CF_3$ | H | |
| 2.041 | 2-Cl | 6-Cl | H | n-$C_3H_7$ | $CF_3$ | H | |
| 2.042 | 2-Cl | 6-Cl | H | i-$C_3H_7$ | $CF_3$ | H | |
| 2.043 | 2-Cl | 6-Cl | H | $CH_3$ | phenyl | H | |
| 2.044 | 2-Cl | 6-Cl | H | $CF_3$ | H | H | |
| 2.045 | 2-Cl | 6-Cl | H | H | $CF_3$ | H | |
| 2.046 | 2-Cl | 6-Cl | H | $CH_2OCH_3$ | $CF_3$ | H | |
| 2.047 | 2-Cl | 6-Cl | H | $CH_3$ | $CF_2Cl$ | H | m.p. 113–116° C. |

TABLE 2-continued

Compounds of formula (II)

$$\text{Ar-NH-Pyridine with } R_1, R_2, R_3 \text{ on phenyl and } R_4, R_5, R_6 \text{ on pyridine}$$

| Comp. No. | $R_1$ | $R_2$ | $R_3$ | $R_4$ | $R_5$ | $R_6$ | Physical data |
|---|---|---|---|---|---|---|---|
| 2.048 | 2-Cl | 6-Cl | H | $C_2H_5$ | $CF_2Cl$ | H | |
| 2.049 | 2-Cl | 6-Cl | H | $CH_3$ | $CHF_2$ | H | |
| 2.050 | 2-Cl | 6-Cl | H | $CH_3$ | $CHCl_2$ | H | |
| 2.051 | 2-Cl | 6-Cl | H | $CH_3$ | Cl | $CH_3$ | |
| 2.052 | 2-Cl | 6-Cl | H | Cl | $CH_3$ | H | |
| 2.053 | 2-Cl | 6-$CH_3$ | H | $CH_3$ | $CF_3$ | CN | |
| 2.054 | 2-Cl | 6-$CH_3$ | H | $CH_3$ | $CF_3$ | H | oil |
| 2.055 | 2-Cl | 6-$CH_3$ | H | $C_2H_5$ | $CF_3$ | H | |
| 2.056 | 2-Cl | 6-$CH_3$ | H | $i\text{-}C_3H_7$ | $CF_3$ | H | |
| 2.057 | 2-Cl | 6-$CH_3$ | H | $CH_3$ | $CF_2Cl$ | H | m.p. 123–124° C. |
| 2.058 | 2-Cl | 6-$CH_3$ | H | $CH_3$ | $CHF_2$ | H | |
| 2.059 | 2-Cl | 6-$CH_3$ | H | $C_2H_5$ | $CF_2Cl$ | H | |
| 2.060 | 2-Cl | 6-F | H | $CH_3$ | $CF_3$ | H | |
| 2.061 | 2-Cl | 6-F | H | $C_2H_5$ | $CF_3$ | H | |
| 2.062 | 2-Cl | 6-F | H | $i\text{-}C_3H_7$ | $CF_3$ | H | |
| 2.063 | 2-Cl | 6-F | H | $CH_3$ | $CH_3$ | H | |
| 2.064 | 2-Cl | 6-Cl | 3-$CH_3$ | $CH_3$ | $CF_3$ | H | |
| 2.065 | 2-Cl | 6-Cl | 3-$CH_3$ | $C_2H_5$ | $CF_3$ | H | |
| 2.066 | 2-Cl | 6-Cl | 3-$CH_3$ | $CF_3$ | $CH_3$ | H | |
| 2.067 | 2-Cl | 6-Cl | 3-Cl | $CH_3$ | $CF_3$ | H | |
| 2.068 | 2-Cl | 6-Cl | 3-Cl | Cl | $CH_3$ | H | |
| 2.069 | 2-Cl | 5-F | H | $CH_3$ | $CF_3$ | H | |
| 2.070 | 2-Cl | 5-F | H | $C_2H_5$ | $CF_3$ | H | |
| 2.071 | 2-F | 5-F | H | $CH_3$ | Cl | H | |
| 2.072 | 2-F | 5-F | H | $CH_3$ | $CF_3$ | H | m.p. 74° C. |
| 2.073 | 2-F | 5-F | H | $CF_3$ | $CH_3$ | H | |
| 2.074 | 2-F | 5-F | H | $C_2H_5$ | $CF_3$ | H | |
| 2.075 | 2-F | 5-F | H | $i\text{-}C_3H_7$ | $CF_3$ | H | |
| 2.076 | 2-F | 5-F | H | $CH_3$ | $CF_2Cl$ | H | |
| 2.077 | 2-F | 5-F | H | $CH_3$ | $CHF_2$ | H | |
| 2.078 | 2-F | 5-F | H | $CH_3$ | $C_2F_5$ | H | |
| 2.079 | 2-F | 6-F | H | $CH_3$ | $CF_3$ | H | m.p. 132 C. |
| 2.080 | 2-F | 6-F | H | $CF_3$ | $CH_3$ | H | |
| 2.081 | 2-F | 6-F | H | $C_2H_5$ | $CF_3$ | H | |
| 2.082 | 2-$NO_2$ | H | H | $CH_3$ | $CF_3$ | H | m.p. 107–108° C. |
| 2.083 | 2-$NO_2$ | H | H | $C_2H_5$ | $CF_3$ | H | m.p. 87° C. |
| 2.084 | 2-$NO_2$ | H | H | $i\text{-}C_3H_7$ | $CF_3$ | H | m.p. 68–69° C. |
| 2.085 | 2-$NO_2$ | H | H | $n\text{-}C_3H_7$ | $CF_3$ | H | m.p. 68° C. |
| 2.086 | 2-$NO_2$ | H | H | $i\text{-}C_4H_9$ | $CF_3$ | H | |
| 2.087 | 2-$NO_2$ | H | H | $s\text{-}C_4H_9$ | $CF_3$ | H | |
| 2.088 | 2-$NO_2$ | H | H | $t\text{-}C_4H_9$ | $CF_3$ | H | |
| 2.089 | 2-$NO_2$ | H | H | $n\text{-}C_4H_9$ | $CF_3$ | H | |
| 2.090 | 2-$NO_2$ | H | H | $CH_3$ | $C_2F_5$ | H | |
| 2.091 | 2-$NO_2$ | H | H | $C_2H_5$ | $C_2F_5$ | H | |
| 2.092 | 2-$NO_2$ | H | H | $CH_3$ | $CF_2Cl$ | H | m.p. 114–115° C. |
| 2.093 | 2-$NO_2$ | H | H | $C_2H_5$ | $CF_2Cl$ | H | |
| 2.094 | 2-$NO_2$ | H | H | $CH_3$ | $CHF_2$ | H | m.p. 128–129° C. |
| 2.095 | 2-$NO_2$ | H | H | $C_2H_5$ | $CHF_2$ | H | |
| 2.096 | 2-$NO_2$ | H | H | $CH_3$ | $CHCl_2$ | H | |
| 2.097 | 2-$NO_2$ | H | H | $C_2H_5$ | $CHCl_2$ | H | |
| 2.098 | 2-$NO_2$ | H | H | $CH_2OCH_3$ | $CF_3$ | H | |
| 2.099 | 2-$NO_2$ | H | H | $CF_3$ | $CH_3$ | H | m.p. 123° C. |
| 2.100 | 2-$NO_2$ | H | H | $CF_3$ | H | H | m.p. 109° C. |
| 2.101 | 2-$NO_2$ | H | H | H | $CF_3$ | H | m.p. 99° C. |
| 2.102 | 2-$NO_2$ | H | H | $CH_3$ | $CH_3$ | H | m.p. 87° C. |
| 2.103 | 2-$NO_2$ | H | H | $CH_3$ | $CF_3$ | CN | m.p. 151° C. |
| 2.104 | 2-$NO_2$ | H | H | $CH_3$ | $CF_3$ | $NO_2$ | |
| 2.105 | 2-$NO_2$ | H | H | $CH_3$ | $CF_3$ | Cl | |
| 2.106 | 2-$NO_2$ | H | H | $C_2H_5$ | $CF_3$ | CN | |
| 2.107 | 2-$NO_2$ | H | H | $CH_3$ | $CF_3$ | $COOCH_3$ | |
| 2.108 | 2-$NO_2$ | H | H | $O\text{—}CH_3$ | $CF_3$ | H | |
| 2.109 | 2-$NO_2$ | H | H | $O\text{—}CH_3$ | $CH_3$ | H | |
| 2.110 | 2-$NO_2$ | H | H | CN | $CH_3$ | H | |
| 2.111 | 2-$NO_2$ | H | H | Cl | $CH_3$ | H | m.p. 122° C. |
| 2.112 | 2-$NO_2$ | H | H | $CH_3$ | Cl | H | |
| 2.113 | 2-$NO_2$ | 6-F | H | $CH_3$ | $CF_3$ | H | m.p. 95–103° C. |
| 2.114 | 2-$NO_2$ | 6-F | H | $C_2H_5$ | $CF_3$ | H | |
| 2.115 | 2-$NO_2$ | 6-F | H | $CF_3$ | $CH_3$ | H | |
| 2.116 | 2-$NO_2$ | 6-F | H | Cl | $CH_3$ | H | |
| 2.117 | 2-$NO_2$ | 6-F | H | $CH_3$ | $CH_3$ | H | |
| 2.118 | 2-$NO_2$ | 6-Cl | H | $CH_3$ | $CF_3$ | H | |
| 2.119 | 2-$NO_2$ | 6-Cl | H | $C_2H_5$ | $CF_3$ | H | |

TABLE 2-continued

Compounds of formula (II)

$$\text{(Ar)}-NH-\text{(Pyridine with } R_4, R_5, R_6\text{)}$$

where the aryl ring bears $R_1, R_2, R_3$ and the pyridine bears $R_4, R_5, R_6$.

| Comp. No. | $R_1$ | $R_2$ | $R_3$ | $R_4$ | $R_5$ | $R_6$ | Physical data |
|---|---|---|---|---|---|---|---|
| 2.120 | 2-NO$_2$ | 6-Cl | H | CH$_3$ | CF$_3$ | CN | |
| 2.121 | 2-NO$_2$ | 6-Cl | H | CF$_3$ | CH$_3$ | H | |
| 2.122 | 2-NO$_2$ | 6-CH$_3$ | H | CH$_3$ | CF$_3$ | H | m.p. 129–130° C. |
| 2.123 | 2-NO$_2$ | 6-CH$_3$ | H | C$_2$H$_5$ | CF$_3$ | H | m.p. 85–86° C. |
| 2.124 | 2-NO$_2$ | 6-CH$_3$ | H | i-C$_3$H$_7$ | CF$_3$ | H | |
| 2.125 | 2-NO$_2$ | 6-CH$_3$ | H | i-C$_4$H$_9$ | CF$_3$ | H | |
| 2.126 | 2-NO$_2$ | 6-CH$_3$ | H | CH$_3$ | CF$_2$Cl | H | m.p. 95–98° C. |
| 2.127 | 2-NO$_2$ | 6-CH$_3$ | H | C$_2$H$_5$ | CF$_2$Cl | H | |
| 2.128 | 2-NO$_2$ | 6-CH$_3$ | H | i-C$_3$H$_7$ | CF$_2$Cl | H | |
| 2.129 | 2-NO$_2$ | 6-CH$_3$ | H | i-C$_4$H$_9$ | CF$_2$Cl | H | |
| 2.130 | 2-NO$_2$ | 6-CH$_3$ | H | CH$_3$ | CHF$_2$ | H | m.p. 103° C. |
| 2.131 | 2-NO$_2$ | 6-CH$_3$ | H | C$_2$H$_5$ | CHF$_2$ | H | |
| 2.132 | 2-NO$_2$ | 6-CH$_3$ | H | i-C$_3$H$_7$ | CHF$_2$ | H | |
| 2.133 | 2-NO$_2$ | 6-CH$_3$ | H | i-C$_4$H$_9$ | CHF$_2$ | H | |
| 2.134 | 2-NO$_2$ | 6-CH$_3$ | H | CH$_3$ | CHCl$_2$ | H | |
| 2.135 | 2-NO$_2$ | 6-CH$_3$ | H | C$_2$H$_5$ | CHCl$_2$ | H | |
| 2.136 | 2-NO$_2$ | 6-CH$_3$ | H | i-C$_3$H$_7$ | CHCl$_2$ | H | |
| 2.137 | 2-NO$_2$ | 6-CH$_3$ | H | i-C$_4$H$_9$ | CHCl$_2$ | H | |
| 2.138 | 2-NO$_2$ | 6-CH$_3$ | H | CF$_3$ | CH$_3$ | H | |
| 2.139 | 2-NO$_2$ | 6-CH$_3$ | H | CH$_3$ | CH$_3$ | H | |
| 2.140 | 2-NO$_2$ | 6-CH$_3$ | H | phenyl | CH$_3$ | H | |
| 2.141 | 2-NO$_2$ | 6-CH$_3$ | H | phenyl | CF$_3$ | H | |
| 2.142 | 2-NO$_2$ | 6-CH$_3$ | H | CH$_3$ | CF$_3$ | CN | |
| 2.143 | 2-NO$_2$ | 6-CH$_3$ | H | CH$_3$ | CF$_3$ | COOCH$_3$ | |
| 2.144 | 2-NO$_2$ | 6-CH$_3$ | H | CH$_3$ | CF$_3$ | Cl | |
| 2.145 | 2-NO$_2$ | 6-CH$_3$ | H | CH$_3$ | CF$_3$ | Br | |
| 2.146 | 2-NO$_2$ | 6-CH$_3$ | H | CH$_3$ | Cl | CH$_3$ | |
| 2.147 | 2-NO$_2$ | 6-CH$_3$ | H | CH$_3$ | CF$_3$ | NO$_2$ | |
| 2.148 | 2-NO$_2$ | 6-CH$_3$ | H | Cl | CF$_3$ | H | |
| 2.149 | 2-NO$_2$ | 6-CH$_3$ | H | Br | CF$_3$ | H | |
| 2.150 | 2-NO$_2$ | 6-CH$_3$ | H | O—CH$_3$ | CF$_3$ | H | |
| 2.151 | 2-NO$_2$ | 5-F | H | CH$_3$ | CF$_3$ | H | m.p. 108° C. |
| 2.152 | 2-NO$_2$ | 5-F | H | CH$_3$ | CF$_3$ | CN | |
| 2.153 | 2-NO$_2$ | 5-F | H | C$_2$H$_5$ | CF$_3$ | H | |
| 2.154 | 2-NO$_2$ | 5-F | H | CF$_3$ | CF$_3$ | H | |
| 2.155 | 2-NO$_2$ | 5-F | H | CH$_3$ | CH$_3$ | H | |
| 2.156 | 2-NO$_2$ | 5-F | H | C$_2$H$_5$ | CH$_3$ | H | |
| 2.157 | 2-NO$_2$ | 5-F | H | CF$_3$ | CH$_3$ | H | |
| 2.158 | 2-NO$_2$ | 5-F | H | Cl | CF$_3$ | H | |
| 2.159 | 2-NO$_2$ | 5-F | H | Cl | CH$_3$ | H | |
| 2.160 | 2-OCF$_3$ | H | H | CF$_3$ | CH$_3$ | H | |
| 2.161 | 2-OCF$_3$ | H | H | CH$_3$ | CF$_3$ | H | |
| 2.162 | 2-CN | H | H | CH$_3$ | CF$_3$ | H | |
| 2.163 | 2-CN | H | H | C$_2$H$_5$ | CF$_3$ | H | |
| 2.164 | 2-NO$_2$ | 5-Cl | H | CH$_3$ | CF$_3$ | H | |
| 2.165 | 2-NO$_2$ | 5-Cl | H | CF$_3$ | CH$_3$ | H | |
| 2.166 | 2-NO$_2$ | 5-CH$_3$ | H | CH$_3$ | CF$_3$ | H | |
| 2.167 | 3-Cl | 5-Cl | H | CH$_3$ | CF$_3$ | H | m.p. 70–72° C. |
| 2.168 | 3-Cl | 5-Cl | H | CH$_3$ | CH$_3$ | H | |
| 2.169 | 3-F | H | H | CH$_3$ | CF$_3$ | H | |
| 2.170 | 3-F | H | H | CF$_3$ | CH$_3$ | H | |
| 2.171 | 3-F | H | H | CH$_3$ | CF$_3$ | CN | |
| 2.172 | 3-F | H | H | CH$_3$ | CH$_3$ | H | |
| 2.173 | 3-F | H | H | CH$_3$ | CH$_3$ | CN | |
| 2.174 | 3-Cl | H | H | CH$_3$ | CF$_3$ | H | |
| 2.175 | 3-CF$_3$ | H | H | CH$_3$ | CF$_3$ | H | |
| 2.176 | 3-F | 5-F | H | CH$_3$ | CF$_3$ | H | |
| 2.177 | 2-NO$_2$ | H | H | CF$_3$ | CF$_3$ | H | m.p. 138–139° C. |
| 2.178 | 2-OCH$_3$ | H | H | CH$_3$ | CF$_3$ | H | $n_D^{20}$ 1.5486 |
| 2.179 | 2-NO$_2$ | H | H | Cl | CF$_3$ | H | m.p. 93–96° C. |
| 2.180 | H | H | H | Cl | CF$_3$ | H | |
| 2.181 | 2-Cl | 6-Cl | H | Cl | CF$_3$ | H | m.p. 113–114° C. |
| 2.182 | 2-NO$_2$ | 6-CH$_3$ | H | Cl | CF$_3$ | H | m.p. 160–161° C. |
| 2.183 | 2-Cl | H | H | CH$_3$ | CF$_2$CL | H | m.p. 62–64° C. |
| 2.184 | 2-Cl | H | H | C$_2$H$_5$ | CF$_2$Cl | H | |
| 2.185 | 2-Cl | H | H | CH$_3$ | C$_2$H | H$_5$ | |
| 2.186 | 2-Br | H | H | CH$_3$ | CF$_2$Cl | H | m.p. 61–62° C. |
| 2.187 | 2-Br | H | H | C$_2$H$_5$ | CF$_2$Cl | H | |
| 2.188 | 2-Br | H | H | CH$_3$ | CHF$_2$ | H | |
| 2.189 | 2-Br | H | H | CH$_3$ | C$_2$F$_5$ | H | |
| 2.190 | 2-CF$_3$ | H | H | CH$_3$ | CF$_2$Cl | H | Fp. 53–55° C. |
| 2.191 | 2-CF$_3$ | H | H | CH$_3$ | CHF$_2$ | H | |

TABLE 2-continued

Compounds of formula (II)

$$\text{Ar-NH-Pyridine}$$ with substituents $R_1, R_2, R_3$ on phenyl and $R_4, R_5, R_6$ on pyridine

| Comp. No. | $R_1$ | $R_2$ | $R_3$ | $R_4$ | $R_5$ | $R_6$ | Physical data |
|---|---|---|---|---|---|---|---|
| 2.192 | 2-Cl | 6-Cl | H | $OCH_3$ | $CF_3$ | H | $n_D^{25}$ 1.5600 |
| 2.193 | 2-Cl | 6-Cl | H | $C_3H_7(i)$ | $CF_2Cl$ | H | |
| 2.194 | 2-Cl | 6-Cl | H | $CH_3$ | $C_2F_5$ | H | |
| 2.195 | 2-Cl | 6-Cl | H | $CH_3$ | $CFCl_2$ | H | |
| 2.196 | 2-Cl | 5-Cl | H | $CH_3$ | $CF_2Cl$ | H | m.p. 101–102° C. |
| 2.197 | 2-Cl | 5-Cl | H | $C_2H_5$ | $CF_2Cl$ | H | |
| 2.198 | 2-$OCHF_2$ | 6-$CH_3$ | H | $CH_3$ | $CF_3$ | H | |
| 2.199 | 2-$OCHF_2$ | 6-$CH_3$ | H | $CH_3$ | $CF_2Cl$ | H | m.p. 84–85° C. |
| 2.200 | 2-$OCHF_2$ | 6-$CH_3$ | H | $C_2H_5$ | $CF_2Cl$ | H | |
| 2.201 | 2-$OCHF_2$ | 6-$CH_3$ | H | $C_3H_7(i)$ | $CF_2Cl$ | H | |
| 2.202 | 2-$OCHF_2$ | 6-$CH_3$ | H | $CH_3$ | $CHF_2$ | H | |
| 2.203 | 2-$OCHF_2$ | 6-$CH_3$ | H | $CH_3$ | $C_2F_5$ | H | |
| 2.204 | 2-$OCHF_2$ | 6-$CH_3$ | H | $C_2H_5$ | $CF_3$ | H | |
| 2.205 | 2-$OCHF_2$ | 6-$CH_3$ | H | $C_3H_7(i)$ | $CF_3$ | H | |
| 2.206 | 2-$NO_2$ | H | H | F | $CH_3$ | H | m.p. 134° C. |
| 2.207 | 2-$NO_2$ | H | H | $CF_3$ | H | $CF_3$ | m.p. 118–119° C. |
| 2.208 | 2-$NO_2$ | H | H | $CH_3$ | $CH_3$ | CN | m.p. 199–200° C. |
| 2.209 | 2-$NO_2$ | H | H | $CH_3$ | $CH_3$ | H | |
| 2.210 | 2-$NO_2$ | H | H | $CF_3$ | H | CN | m.p. 132–133° C. |
| 2.211 | 2-$NO_2$ | H | H | $C_3H_7(i)$ | $CF_2Cl$ | H | |
| 2.212 | 2-$NO_2$ | H | H | $CH_3$ | $CFCl_2$ | H | |
| 2.213 | 2-$NO_2$ | H | H | $C_2H_5$ | $CFCl_2$ | H | |
| 2.214 | 2-$NO_2$ | 6-F | H | $CH_3$ | $CF_2Cl$ | H | m.p. 68–69° C. |
| 2.215 | 2-$NO_2$ | 6-F | H | $C_2H_5$ | $CF_2Cl$ | H | |
| 2.216 | 2-$NO_2$ | 6-F | H | $C_3H_7(i)$ | $CF_2Cl$ | H | |
| 2.217 | 2-$NO_2$ | 6-F | H | $CH_3$ | $C_2F_5$ | H | |
| 2.218 | 2-$NO_2$ | 6-F | H | $C_2H_5$ | $C_2H_5$ | H | |
| 2.219 | 2-$NO_2$ | 6-F | H | $CH_3$ | $CHF_2$ | H | |
| 2.220 | 2-$NO_2$ | 6-F | H | $C_2H_5$ | $CHF_2$ | H | |
| 2.221 | 2-$NO_2$ | 6-F | H | $CH_3$ | $CFCl_2$ | H | |
| 2.222 | 2-$NO_2$ | 6-Cl | H | $CH_3$ | $CF_2Cl$ | H | |
| 2.223 | 2-$NO_2$ | 6-Cl | H | $C_2H_5$ | $CF_2Cl$ | H | |
| 2.224 | 2-$NO_2$ | 6-$CH_3$ | H | $CH_3$ | $CFCl_2$ | H | |
| 2.225 | 2-$NO_2$ | 6-$CH_3$ | H | $CH_3$ | $C_2F_5$ | H | |
| 2.226 | 2-$NO_2$ | 6-$CH_3$ | H | $C_2H_5$ | $C_2F_5$ | H | |
| 2.227 | 2-$NO_2$ | 5-Cl | H | $CH_3$ | $CF_2Cl$ | H | |
| 2.228 | 2-$NO_2$ | 5-Cl | H | $C_2H_5$ | $CF_2Cl$ | H | |
| 2.229 | 2-$NO_2$ | 5-Cl | H | $CH_3$ | $CHF_2$ | H | |
| 2.230 | 2-$NO_2$ | H | H | $CH_3$ | CN | H | |
| 2.231 | 2-$NO_2$ | 6-$C_2H_5$ | H | $CH_3$ | $CF_3$ | H | m.p. 106–108° C. |
| 2.232 | 2-$NO_2$ | 6-$C_2H_5$ | H | $CH_3$ | $CF_2Cl$ | H | m.p. 110–113° C. |
| 2.233 | 2-$NO_2$ | 6-$C_2H_5$ | H | $C_2H_5$ | $CF_3$ | H | |

B. BIOLOGICAL EXAMPLES

Example B1: Preemergence Herbicidal Activity

Immediately after sowing the test plants in pots in a greenhouse, the surface of the soil is treated with an aqueous dispersion of the test compound obtained from a 25% emulsifiable concentrate. The rate of application is 4 kg of test compound per hectare. The pots are kept in the greenhouse at 22°–25° C. and 50–70% relative humidity, and the test is evaluated 3 weeks later.

The herbicidal activity is assessed in accordance with a rating from 1 to 9 (1=total damage to the test plant, 9=no herbicidal effect on the test plant) and using an untreated control group for comparison purposes.

Ratings from 1 to 4 (especially from 1 to 3) are indicative of a good to very good herbicidal activity. The results are reported in Table 3:

TABLE 3

| Comp. No. | Preemergence herbicidal activity | | | |
|---|---|---|---|---|
| | Test plant | | | |
| | Avena | Sinapis | Setaria | Stellaria |
| 1.083 | 1 | 2 | 1 | 1 |

Example B2: Postemergence Herbicidal Activity

A number of weeds, monocots as well as dicots, are sprayed postemergence in the 4- to 6-leaf stage with an aqueous dispersion at a rate of application of 4 kg of test compound per hectare and kept at 24°–26° C. and 45–60% relative humidity. The test is evaluated 15 days after treatment. The herbicidal activity is assessed in the same manner as in Example B1. The individual results are reported in Table 4:

| Comp. | Test plant No. | | | | | |
|---|---|---|---|---|---|---|
| | Setaria | Stellaria | Lolium | Solanum | Avena | Sinapis |
| 1.083 | 4 | 3 | 3 | 4 | 3 | 2 |

Example B3: Herbicidal Activity Against Weeds in Water Rice

The aquatic weeds are sown in plastic beakers (surface 60 cm², volume 500 ml). After sowing, the beakers are filled with water up to the surface of the soil. Three days after sowing, the water level is raised to slightly above the surface of the soil (3-5 mm). Application is made 3 days after sowing by spraying the beakers with an aqueous emulsion of the test compound. The rate of application corresponds to a concentration of 4 kg of test compound per hectare (concentration of the spray mixture: ca. 550 l/ha). The beakers are then kept in the greenhouse under optimum growth conditions for the weeds, i.e. at 25°-30° and high humidity, Evaluation of the test is made 2-3 weeks after application, depending on the growth rate and species of plant. The state of the plants is assessed in accordance with the rating employed in Example B1. The individual results are reported in Table 5.

TABLE 5

| Comp. | Herbicidal action in paddy rice | |
|---|---|---|
| | Test plant | |
| No. | Echinochloa | Monocharia |
| 1.083 | 1 | 1 |

Example 4: Growth Inhibition of Cereals

The plants (e.g. summer barley of the Iban variety) are sown in 15 cm plastic pots containing sterilised country soil and cultivated in a climatic chamber at a day temperature of 10°-15° C. and a night temperature of 5°-10° C. The light exposure time is 13.5 hours per day.

Application with 0.3 to 3 kg of test compound per hectare (normally formulated as 25% aqueous spray mixture) is made ca. 34 days after sowing and thinning out to 4 plants per pot. The amount of water is ca. 500 l/ha. After application, the plants are kept in a greenhouse at a day temperature of at least 10° C. The light exposure time is at least 13.5 hours per day.

Evaluation is made ca. 28 days after the treatment by assessing the height of the new growth. The tested compounds of formula I effect a reduction of new growth as compared with untreated control plants.

Example B5: Growth Inhibition of Grasses with Clover

A mixture of grasses (for example Poa, Festuca, Lolium, Bromus, Cynosurus) and clover is sown in 15 cm plastic pots containing sterilised country soil and kept in a greenhouse at a day temperature of 21° C. and a night temperature of 17° C. The light exposure time is 13.5 hours per day at a light intensity of at least 7000 lux. The plants are then cut back postemergence weekly to a height of ca. 6 cm. Application with 0.3 to 3 kg of test compound per hectare (normally formulated as 25% aqueous spray mixture) is made ca. 42 days after sowing and 1 day after the last cut. The amount of water is ca. 500 l/ha.

Evaluation is made ca. 3 weeks after the treatment by measuring the height of the new growth. The tested compounds of formula I effect a reduction of new growth as compared with untreated control plants.

Example B6: Growth Inhibition of Cereals

Summer barley (*Hordeum vulgare*) and summer rye (*Secale*) are sown in sterilised soil in plastic beakers in a greenhouse and watered as required. The cereal shoots are treated ca. 21 days after sowing with an aqueous spray mixture of a compound of Table 1. The growth of the cereals is evaluated 21 days after application. A comparison with untreated controls shows that the new growth of the treated plants is reduced and that the diameter of the stalks of some of the plants has increased.

Example B7: Growth Inhibition of Grasses

In a greenhouse, the grasses *Lolium perenne*, *Poa pratensis*, *Festuca ovina*, *Dactylis glomerata* and *Cynodon dactylon* are sown in plastic dishes filled with an earth-/peat/sand mixture (6:3:1) and watered as required. The emergent grasses are cut back weekly to a height of 4 cm and, about 50 days after sowing and 1 day after the last cut are sprayed with an aqueous spray mixture of a compound of Table 1. The concentration of test compound corresponds to a rate of application of up to 500 g of test compound per hectare. The growth of the grasses is evaluated 21 days after application.

The test compounds of Table 1 effect a reduction of new growth as compared with untreated controls.

FORMULATION EXAMPLES

Example F1: Formulation Examples for Compounds of Formula I (throughout, percentages are by weight)

| a) Emulsifiable concentrates | a) | b) | c) |
|---|---|---|---|
| a compound of Table 1 | 20% | 40% | 50% |
| calcium dodecylbenzenesulfonate | 5% | 8% | 5.8% |
| castor oil polyethylene glycol ether (36 mol of ethylene oxide) | 5% | — | — |
| tributylphenol polyethylene glycol ether (30 mol of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| b) Solutions | a) | b) | c) |
|---|---|---|---|
| a compound of Table 1 | 80% | 10% | 5% |
| ethylene glycol monomethyl ether | 20% | — | — |
| polyethylene glycol (mol. wt. 400) | — | 70% | — |
| N-methyl-2-pyrrolidone | — | 20% | 5% |
| epoxidised coconut oil | — | — | 90% |

These solutions are suitable for application in the form of microdrops.

| c) Granulates | a) | b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| d) Dusts | a) | b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| e) Wettable powders | a) | b) |
|---|---|---|
| a compound of Table 1 | 20% | 60% |
| sodium lignosulfonate | 5% | 5% |
| sodium lauryl sulfate | 3% | 6% |
| octylphenol polyethylene glycol ether (7-8 moles of ethylene oxide) | — | 2% |
| highly dispersed silicic acid | 5% | 27% |
| kaolin | 67% | |

The active ingredient is thoroughly mixed with the adjuvants and the mixture is thoroughly ground in a suitable mill, affording wettable powders which can be diluted with water to give suspensions of the desired concentration.

| f) Extruder granulate | |
|---|---|
| a compound of Table 1 | 10% |
| sodium ligninsulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| g) Coated granulate | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| h) Suspension concentrate | |
|---|---|
| a compound of Table 1 | 40% |
| ethylene glycol | 10% |
| nonylphenol polyethylene glycol (15 mol of ethylene oxide) | 6% |
| sodium ligninsulfonate | 10% |
| carboxymethylcellulose | 1% |
| 37% aqueous formaldehyde solution | 0.2% |
| silicone oil in the form of a 75% aqueous emulsion | 0.8% |
| water | ad 100% |

The active ingredient is intimately mixed with the adjuvants, giving a suspension concentrate from which suspensions of any desired concentration can be obtained by dilution with water.

What is claimed is:

1. A herbicidal or plant growth regulating composition which contains, as active ingredient, at least an effective amount of a urea of formula I

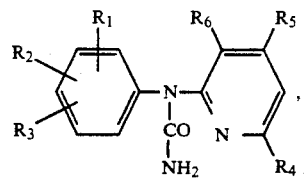

wherein $R_1$, $R_2$ and $R_3$ are each independently of one another hydrogen; nitro; cyano; halogen; $C_1$-$C_4$alkyl; $C_1$-$C_4$alkyl-$S(O)_n$-; $C_1$-$C_4$alkoxy; $C_1$-$C_4$haloalkyl; $C_1$-$C_4$haloalkoxy; $C_1$-$C_4$haloalkyl-$S(O)_n$-; $C_1$-$C_4$alkoxycarbonyl; $C_1$-$C_4$alkylcarbonyl; carbamoyl; mono-$C_1$-$C_4$alkylcarbamoyl; or di-$C_1$-$C_4$alkylcarbamoyl;

$R_4$ and $R_5$ are each independently of the other hydrogen; $C_1$-$C_4$alkyl; $C_1$-$C_4$alkyl-$S(O)_n$-; $C_1$-$C_4$alkoxy; $C_1$-$C_4$haloalkyl; $C_1$-$C_4$haloalkoxy; $C_1$-$C_4$haloalkyl-$S(O)_n$-; unsubstituted phenyl or phenyl which is substituted by one to three identical or different members of the group consisting of $C_1$-$C_4$alkyl, halogen, $C_1$-$C_4$alkoxy, $C_1$-$C_4$haloalkyl, nitro and cyano; furanyl; thiophenyl; $C_3$-$C_6$cycloalkyl; $C_1$-$C_4$alkoxycarbonyl; $C_1$-$C_4$alkoxy-$C_1$-$C_4$alkyl; $C_1$-$C_4$alkoxycarbonyl-$C_1$-$C_4$alkyl; $C_1$-$C_4$alkylcarbonyl-$C_1$-$C_4$alkyl; $C_3$-$C_4$alkenyloxycarbonyl-$C_1$-$C_4$alkyl; $C_3$-$C_4$alkynyloxycarbonyl-$C_1$-$C_4$alkyl; halogen; or cyano; and $R_6$ is hydrogen; $C_1$-$C_4$alkyl; nitro; cyano; halogen; $C_1$-$C_4$alkoxycarbonyl; $C_1$-$C_4$haloalkyl; and n is 0, 1 or 2, or a salt thereof with an acid, base or chelating agent, together with a carrier and a surfactant.

2. A composition according to claim 1, which contains as active ingredient a compound of formula Ia which is unsubstituted in the 4-position of the phenyl ring

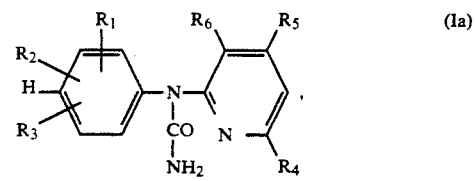

3. A composition according to claim 1, which contains as active ingredient a compound of formula Ia

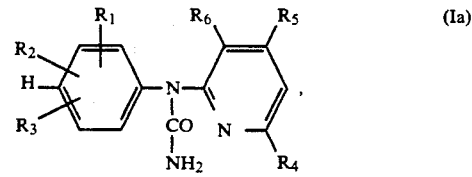

wherein $R_1$, $R_2$ and $R_3$ are each independently of one another hydrogen; nitro; halogen; $C_1$-$C_4$alkyl; $C_1$-$C_4$haloalkyl; $C_1$-$C_4$alkoxy; or $C_1$-$C_4$haloalkoxy;

$R_4$ and $R_5$ are each independently of each other hydrogen; cyano; halogen; $C_1$-$C_4$alkyl; $C_1$-$C_4$alkoxy;

$C_1-C_4$haloalkyl; $C_1-C_4$alkoxy-$C_1-C_4$alkyl; phenyl; or furanyl; and $R_6$ is hydrogen; cyano; nitro; halogen; or $C_1-C_4$alkoxycarbonyl.

4. A composition according to claim 1, which contains as active ingredient a compound of formula Ia

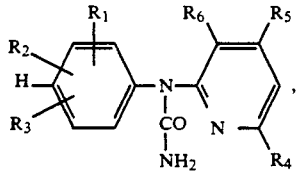

wherein $R_1$ is hydrogen; nitro; halogen; $C_1-C_4$haloalkyl; or $C_1-C_4$haloalkoxy;

$R_2$ is hydrogen; halogen; or $C_1-C_4$alkyl;

$R_3$ is hydrogen; $C_1-C_4$alkyl; or halogen;

$R_4$ cyano; halogen; $C_1-C_4$alkyl; $C_1-C_4$alkoxy; $C_1-C_4$haloalkyl; $C_1-C_4$alkoxy-$C_1-C_4$alkyl; phenyl; or furanyl;

$R_5$ is halogen; $C_1-C_4$alkyl; $C_1-C_4$haloalkyl; or phenyl; and $R_6$ is hydrogen; cyano; nitro; halogen; or $C_1-C_4$alkoxycarbonyl.

5. A composition according to claim 1, which contains as active ingredient a compound of formula Ia

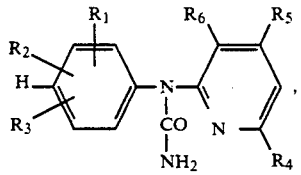

wherein $R_1$ is hydrogen; fluoro; chloro; bromo; iodo; nitro; trifluoromethyl; methoxy; trifluoromethoxy; or difluoromethoxy;

$R_2$ is hydrogen; fluoro; chloro; or methyl;

$R_3$ is hydrogen; chloro; or methyl;

$R_4$ chloro; bromo; $C_1-C_4$alkyl; cyano; methoxy; trifluoromethyl; methoxymethyl; phenyl; or furanyl;

$R_5$ is chloro; methyl; trifluoromethyl; chlorodifluoromethyl; difluoromethyl; dichloromethyl; or pentafluoroethyl; and $R_6$ is hydrogen; cyano; nitro; chloro; bromo; or methoxycarbonyl.

6. A composition according to claim 1, which contains as active ingredient a compound of formula $Ia^1$, $Ia^2$, $Ia^3$, $Ia^4$, $Ia^5$ or $Ia^6$

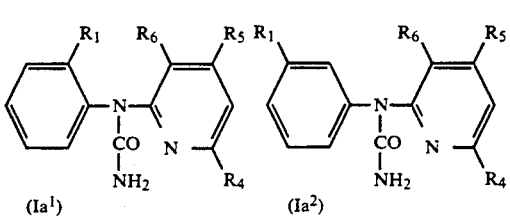

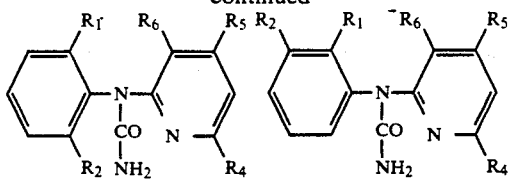

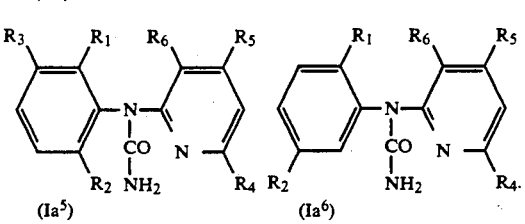

7. A composition according to claim 2, which contains as active ingredient a compound of formula Ia, wherein $R_4$ and $R_5$ are each independently of the other $C_1-C_4$haloalkyl; or $C_1-C_4$alkyl; and $R_6$ is hydrogen.

8. A composition according to claim 6, which contains as active ingredient a compound of formula $Ia^1$ or $Ia^3$, wherein $R_6$ is hydrogen; and $R_4$ and $R_5$ are each independently of the other $C_1-C_4$haloalkyl; or $C_1-C_4$alkyl.

9. A composition according to claim 8, which contains as active ingredient a compound of formula $Ia^1$ or $Ia^3$, wherein $R_1$ is nitro; and $R_4$ and $R_5$ are each independently of the other $C_1-C_4$haloalkyl, or $C_1-C_4$alkyl.

10. A composition of claim 1 in which the carrier is a seed of a useful plant.

11. A urea of formula Ia

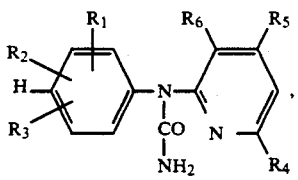

wherein $R_1$ is nitro;

$R_2$ is hydrogen; halogen; or $C_1-C_4$alkyl;

$R_3$ is hydrogen; $C_1-C_4$alkyl; or halogen;

$R_4$ is halogen; $C_1-C_4$alkyl; $C_1-C_4$alkoxy; or $C_1-C_4$alkoxy-$C_1-C_4$alkyl;

$R_5$ is $C_1-C_4$alkyl; or $C_1-C_4$haloalkyl; and $R_6$ is hydrogen.

12. A urea of formula Ia according to claim 11 wherein $R_2$ is hydrogen; fluoro; chloro; or methyl;

$R_3$ is hydrogen; chloro; or methyl;

$R_4$ is chloro; bromo; $C_1-C_4$alkyl; methoxy; or methoxymethyl;

$R_5$ is methyl; trifluoromethyl; chlorodifluoromethyl; difluoromethyl; dichloromethyl; or pentafluoroethyl.

13. A urea of formula $Ia^1$, $Ia^2$, $Ia^3$, $Ia^4$, $Ia^5$ or $Ia^6$ according to claim 11

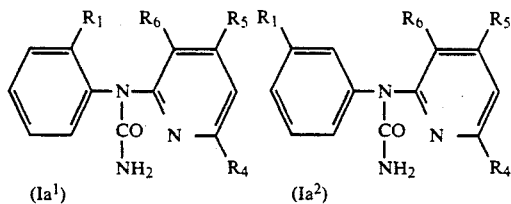
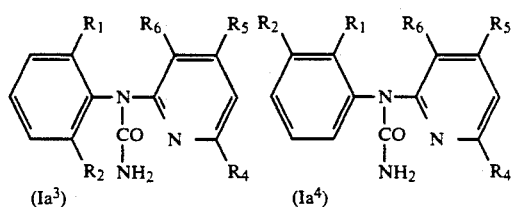
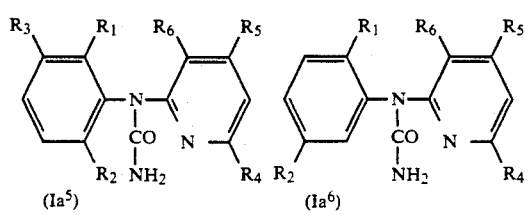

14. A urea of formula Ia according to claim 11, wherein

R$_4$ and R$_5$ are each independently of the other C$_1$-C$_4$alkyl.

15. A urea of formula Ia$^1$ or Ia$^3$ according to claim 13, wherein

R$_4$ and R$_5$ are each independently of the other C$_1$-C$_4$alkyl.

16. A carbamyl chloride of the formula

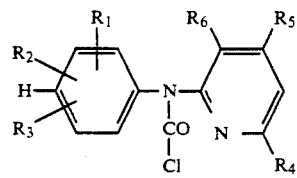

wherein R$_1$ to R$_6$ are as defined for formula I according to claim 11.

17. A halosulfonylurea of formula IV

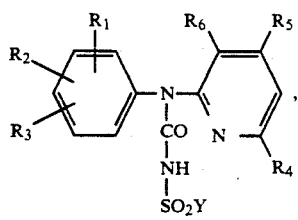

wherein R$_1$ to R$_6$ are as defined for formula I according to claim 1.

18. A method of controlling undesired plant growth, which comprises applying to the plants to be controlled or to the locus thereof a herbicidally effective amount of a compound of formula I

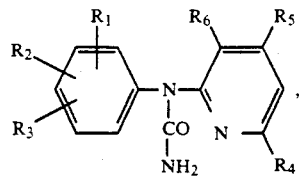

wherein

R$_1$, R$_2$ and R$_3$ are each independently of one another hydrogen; nitro; cyano; halogen; C$_1$-C$_4$alkyl; C$_1$-C$_4$alkyl-S(O)$_n$-; C$_1$-C$_4$alkoxy; C$_1$-C$_4$haloalkyl; C$_1$-C$_4$haloalkoxy; C$_1$-C$_4$haloalkyl-S(O)$_n$-; C$_1$-C$_4$alkoxycarbonyl; C$_1$-C$_4$alkylcarbonyl; carbamoyl; mono-C$_1$-C$_4$alkylcarbamoyl; or di-C$_1$-C$_4$alkylcarbamoyl;

R$_4$ and R$_5$ are each independently of the other hydrogen; C$_1$-C$_4$alkyl; C$_1$-C$_4$alkyl-S(O)$_n$-; C$_1$-C$_4$alkoxy; C$_1$-C$_4$haloalkyl; C$_1$-C$_4$haloalkoxy; C$_1$-C$_4$haloalkyl-S(O)$_n$-; unsubstituted phenyl or phenyl which is substituted by one to three identical or different members of the group consisting of C$_1$-C$_4$alkyl, halogen, C$_1$-C$_4$alkoxy, C$_1$-C$_4$haloalkyl, nitro and cyano; furanyl; thiophenyl; C$_3$-C$_6$cycloalkyl; C$_1$-C$_4$alkoxycarbonyl; C$_1$-C$_4$alkoxy-C$_1$-C$_4$alkyl; C$_1$-C$_4$alkoxycarbonyl-C$_1$-C$_4$alkyl; C$_1$-C$_4$alkylcarbonyl-C$_1$-C$_4$alkyl; C$_3$-C$_4$alkenyloxycarbonyl-C$_1$-C$_4$alkyl; C$_3$-C$_4$alkynyloxycarbonyl-C$_1$-C$_4$alkyl; halogen; or cyano; and R$_6$ is hydrogen; C$_1$-C$_4$alkyl; nitro; cyano; halogen; C$_1$-C$_4$alkoxycarbonyl; C$_1$-C$_4$haloalkyl; and n is 0, 1 or 2, or a salt thereof with an acid.

19. A method according to claim 18 of controlling undesired plant growth pre- or postemergence in crops of useful plants.

20. A method of claim 18 which comprises applying a herbicidally effective amount of a compound of formula Ia which is unsubstituted in the 4-position of the phenyl ring

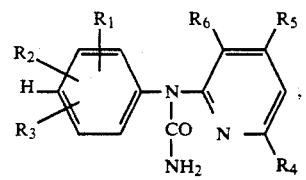

21. A method of claim 20 which comprises applying a herbicidally effective amount of a compound of formula Ia

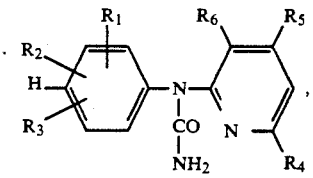

wherein

R$_1$, R$_2$ and R$_3$ are each independently of one another hydrogen; nitro; halogen; C$_1$-C$_4$alkyl; C$_1$-C$_4$haloalkyl; C$_1$-C$_4$alkoxy; or C$_1$-C$_4$haloalkoxy;

R$_4$ and R$_5$ are each independently of each other hydrogen; cyano; halogen; C$_1$-C$_4$alkyl; C$_1$-C$_4$alkoxy;

$C_1$-$C_4$haloalkyl; $C_1$-$C_4$alkoxy-$C_1$-$C_4$alkyl; phenyl; or furanyl; and $R_6$ is hydrogen; cyano; nitro; halogen; or $C_1$-$C_4$alkoxycarbonyl.

22. A method of claim 20 which comprises applying a herbicidally effective amount of a compound of formula Ia

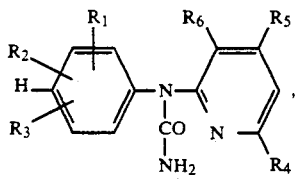

wherein $R_1$ is hydrogen; nitro; halogen; $C_1$-$C_4$haloalkyl; or $C_1$-$C_4$haloalkoxy;

$R_2$ is hydrogen; halogen; or $C_1$-$C_4$alkyl;

$R_3$ is hydrogen; $C_1$-$C_4$alkyl; or halogen;

$R_4$ cyano; halogen; $C_1$-$C_4$alkyl; $C_1$-$C_4$alkoxy; $C_1$-$C_4$haloalkyl; $C_1$-$C_4$alkoxy-$C_1$-$C_4$alkyl; phenyl; or furanyl;

$R_5$ is halogen; $C_1$-$C_4$alkyl; $C_1$-$C_4$haloalkyl; or phenyl; and $R_6$ is hydrogen; cyano; nitro; halogen; or $C_1$-$C_4$alkoxycarbonyl.

23. A method of claim 20 which comprises applying a herbicidally effective amount of a compound of formula Ia

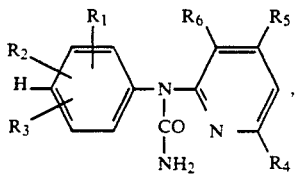

wherein $R_1$ is hydrogen; fluoro; chloro; bromo; iodo; nitro; trifluoromethyl; methoxy; trifluoromethoxy; or difluoromethoxy;

$R_2$ is hydrogen; fluoro; chloro; or methyl;

$R_3$ is hydrogen; chloro; or methyl;

$R_4$ chloro; bromo; $C_1$-$C_4$alkyl; cyano; methoxy; trifluoromethyl; methoxymethyl; phenyl; or furanyl;

$R_5$ is chloro; methyl; trifluoromethyl; chlorodifluoromethyl; difluoromethyl; dichloromethyl; or pentafluoroethyl; and $R_6$ is hydrogen; cyano; nitro; chloro; bromo; or methoxycarbonyl.

24. A method of claim 20 which comprises applying a herbicidally effective amount of a compound of formula Ia$^1$, Ia$^2$, Ia$^3$, Ia$^4$, Ia$^5$ or Ia$^6$

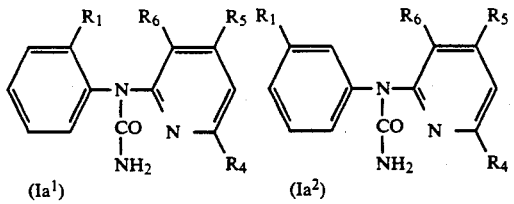

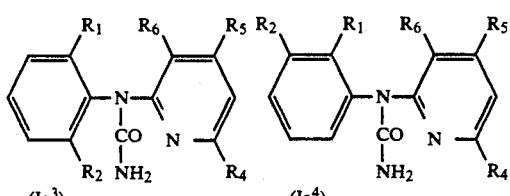

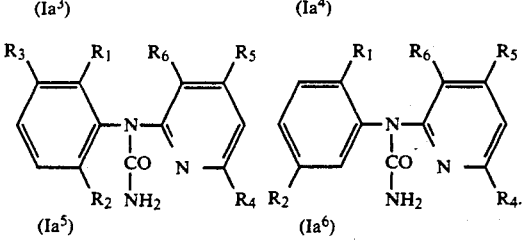

25. A method of claim 20 which comprises applying a herbicidally effect amount of a compound of formula Ia, wherein $R_4$ and $R_5$ are each independently of the other $C_1$-$C_4$haloalkyl; or $C_1$-$C_4$alkyl; and $R_6$ is hydrogen.

26. A method of claim 24 which comprises applying a herbicidally effective amount of a compound of formula Ia$^1$ or Ia$^3$, wherein $R_6$ is hydrogen; and $R_4$ and $R_5$ are each independently of the other $C_1$-$C_4$haloalkyl; or $C_1$-$C_4$alkyl.

27. A method of influencing plant growth, which comprises treating plants or the locus thereof with a plant growth regulating amount of a compound of formula I as claimed in claim 18.

28. A method of claim 26 wherein $R_4$ and $R_5$ are each independently of the other trifluoromethyl or $C_1$-$C_4$alkyl.

* * * * *